United States Patent
Jofuku et al.

(10) Patent No.: US 6,846,669 B1
(45) Date of Patent: Jan. 25, 2005

(54) METHODS FOR IMPROVING SEEDS

(75) Inventors: K. Diane Jofuku, Santa Cruz, CA (US); Jack K. Okamuro, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/879,827

(22) Filed: Jun. 20, 1997

Related U.S. Application Data

(63) Continuation-in-part of application No. 08/700,152, filed on Aug. 20, 1996, now Pat. No. 5,994,622.

(51) Int. Cl.[7] .................. C12N 15/82; C12N 15/29; A01H 1/00; A01H 5/00; A01H 5/10
(52) U.S. Cl. .................. 435/320.1; 536/23.6; 800/260; 800/263; 800/264; 800/298; 800/281; 800/285; 800/286; 800/290
(58) Field of Search .................. 536/23.6; 800/260, 800/263, 264, 298, 281, 285, 286, 290, 250, 205, 255; 435/320.1, 172.3; 47/56

(56) References Cited

U.S. PATENT DOCUMENTS 5,994,622 A * 11/1999 Jofuku et al. ............... 800/260

OTHER PUBLICATIONS

Sharrocks et al (Int. J. Biochem. Cell. Biol. 29:1371–1387), 1997.*
Riechmann et al, "The AP2/EREB family of plant transcription factors", Biological Chemistry 379:156–29, 1998.*
Riechmann et al, "MADS domain proteins in plant development", Biological Chemistry 378:1079–1101, 1997.*
Clarke et al, "Zinc fingers in Caenorhabditis elegans: finding families and probing pathways", Science 282:2018–2022, 1998.*
Jofuku et al, The Plant Cell 6: 1211–1225, 1994.*
*Arabidopsis: An Atlas of Morphology and Development*, Bowman, J. ed. pp351–401 (Springer–Verlag New York, 1994).
Bowman et al., *Development* 119:721–743 (1993).
Bowman et a.l, *Plant Cell* 1:37–52 (1989).
Bowman et al., *Plant Cell* 3:749–758 (1991).
Bowman, *Flowering Newsletter* 14:7–19 (1992).
Bowmann, et al., *Development* 112:1–20 (1991).
Coen & Carpenter, *Plant Cell*, 5:1175–1181 (1993).
Drews et al., *Cell* 65:991–1002 (1991).
Ecker, *Science* 268:667–675 (1995).
Elliot, *Plant Cell* 8:155–168 (1996).
Huala & Sussex, *Plant Cell* 4:901–913 (1992).
Irish & Sussex, *Plant Cell* 2:741–753 (1990).
Klucher, *Plant Cell* 8:137–153 (1996).
Jack et al., *Cell* 68:683–697 (1992).
Jofuku, K., et al., *Plant Cell* 6:1211–1225 (1994).
Komaki et al., *Development* 104:195–203 (1988).
Kunst et al., *Plant Cell* 1:1195–1208 (1989).
Leon–Kloosterziel et al., *Plant Cell* 6:385–392 (1994).
Mandel et al., *Cell* 71:133–143 (1992).
Mizukami and Ma, *Cell* 71:119–131 (1992).
Ohme–Takagi, et al., *Plant Cell* 7:173–182 (1995).
Okamuro et al., *Plant Cell* 5:1183–1193 (1993).
Schultz & Haughn, *Development* 119:745–765 (1993).
Shannon & Meeks–Wagner, *Plant Cell* 5:639–655 (1993).
Weigel, *Plant Cell* 7:388–389 (1995).
Wilson, et al., *Plant Cell* 8:659–671 (1996).

* cited by examiner

*Primary Examiner*—Mary E. Mosher
(74) *Attorney, Agent, or Firm*—Townsend & Townsend & Crew

(57) ABSTRACT

The invention provides methods of modulating seed mass and other traits in plants. The methods involve producing transgenic plants comprising a recombinant expression cassette containing an ADC nucleic acid linked to a plant promoter.

95 Claims, 7 Drawing Sheets

```
              YRG ELEMENT                              RAYD ELEMENT
                                                         α-HELIX
          1              16             31             46             61             76
          +        +     +                     ++
AP2-R1   SSQYRQVTFYRRTGR WESHIWD-------  --CGKQQYLGGFDTA HAAARAYDVAAIKER GVEADINENIDDDD CL
   -R2   SSKYRGVT-LHKCGR WEARMGQFLG----  ---KKYQYLGLFDTE VEAARARAYDKAAIKCN GKDAVINFDPSIYDE EL
ANT-R1   TSQYRGVTRMRWTGR YEAHLWDNSFKKEGH SRKGFQVYDGGYDME EKAARAYDLAALKYW GPSTHTNFSAENYQK KI
   -R2   ASIFRFVTRHHQHGR WQARIGRVAG---- ---NKDLYLQTFGTQ EFAARAYDMAATKER GINAVTNFDITRYDV CR
RAP2.7-R1 SSQYRGVIFYRRTGR WASHIWD-------  --CGKQQVYLGGFDTA HAAARAYDRAIEFR GVDADCNFTNFTLGDYEE DM
   -R2   SSKYRGVT-LHKCGR WEARM---------  QQEIGK          KAKDKAAINTN    GREAVINFEMSSYQN EI wear
CONSENSUS  .S.YRGVT.....GR wesh.........  ....+.vYLG.f... ..AA.AYD.AAik.. G....tNF....Y.. -.
```

FIG. 4A.

```
            YRG ELEMENT                                    RAYD ELEMENT
         1             16              31              46              61              76
EREBP-1  GRHYRGVR-RRPWGM FAAEIRDPAKNG------ ARVWLGTYED EEAAIAYDKAAYRMF GSKKHLNFPLEVANT KQ69
EREBP-2  GRHYRGVR-QRPWGM FAAEIRDPAKNG------ ARVMLGTYED EEAAALAYDKAAYRMR GSKALIPFPHRIGLN EP69
EREBP-3  EVHYRGVR-KRPWGR YAAEIRDPGKKS------ RVWLGTFDTA EEAAKAYDTAAREFR GPKAKTNFPSPTENQ SP68
EREBP-4  KKHYRGVR-QRPWGR FAAEIRDPNRKG------ TRVWLGTFDTA IFAAKAYDRAAFKLR GSKAIVNFPHRIGLN EP69

RAP2.2   KNQYRGIR-QRPNGA NAAEIRDRRXGS------ REWLGTPDTA NEAARAYDAARRIR QTKAKVNEPEEKNPS VV64
RAP2.3   KNVYRGTR-KRPWGR WAAEIRDRRKGV------ RVWLGTFNTA EEAAMAYDVAAKQIR QQKAKLNFPDLHHPP PP68
RAP2.5   EIRYRGVR-KRPWGF YAAKIRDPGKKT------ RVWLGTFDTA KKAARAYDTAARDEF GAKAKTNFPTFLELS DQ68
RAP2.6   PKKYRQVR-QRPWGM WAARIRDPHKAT------ RVWLGTFETA TAAATAYDAAALRFE GSKAKLNFPENVGTQ TI68
RAP2.12  KNQYRGIR-QRPWGR WAAVIRDPREGA------ RIWLGTFKTA FEAARAYDAARRIE GSKPAKVNFREENMKA NS68

TINY     HPVYRGVR-KRNWGM WVSEIREPRKKS------ RIWLGTFPTR EMAARAHDVAALSTR GASPAILNFPDLAGSF PR68
RAP2.1   RKPYRGIR-RRKWGK WVARIRKRNKRS------ RLMLGSYTTD TAAAARAYDVAVEYLR GPSPARLNFPSLLLQE ED68
RAP2.4   TKLYRGVR-QRHWGK WVAKIRLRRNRT------ RLMLGTFDTA ELAALAYDKAAYKIF GDFPARLNFPNLRHNG FH68
RAP2.8   SSKYKGVV-PQPNGK WGAQIYEKHQ------- KVWLGTFNED ELAARSYDTAACREF GRDAVVNFKNVLEDG DL66
RAP2.10  DKPYKGIR-MRKWGK WVARIRKRNKRS------ RIWLGSYSTR EAAARAYDTAVEYLE GPSPARLNFPELLAGV TV68
RAP2.11  KTKKVGVR-QRPSGK WVAKIKDITQKI------ QMWLGTFDTA KEAARAYDFAACLIR GSNIRTNFANHFPNN SQ68

CONSENSUS...yRGvr..R.wG+      waAEird......     R.WLGtf.t.   eeAA+AYD.Aa...+   G..A..NFP......
            i      +        fv    ke                sy              i      v         l
            y
```

FIG. 4B.

```
AP2       R1  -KQMTNLTKEEFVHVLRRQSTGFPRG-  R2
ANT       R1  -EDMMKNMTRQEYVAHLRRKSSGFSRG- R2
RAP2.7    R1  -MKQVQNLSKEEFVRILRRQSTGFSRG- R2
CONSENSUS R1  -..qm.Nlt+eEfVh.lRRqStGFsRG- R2
```

FIG. 4E.

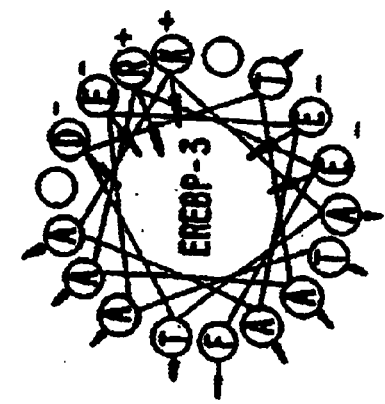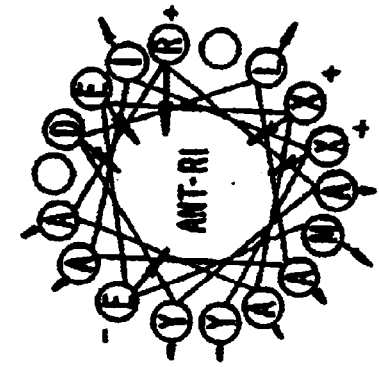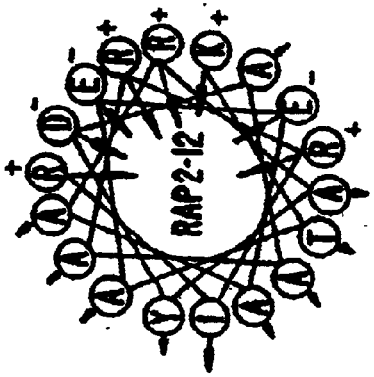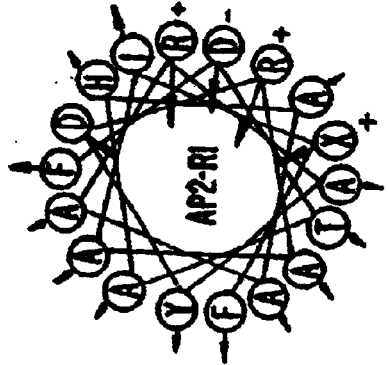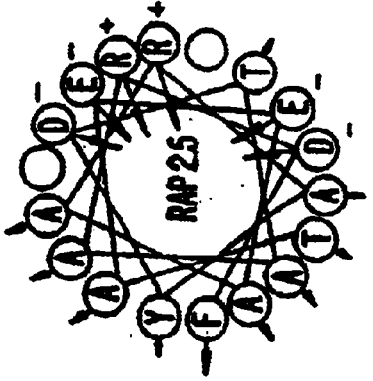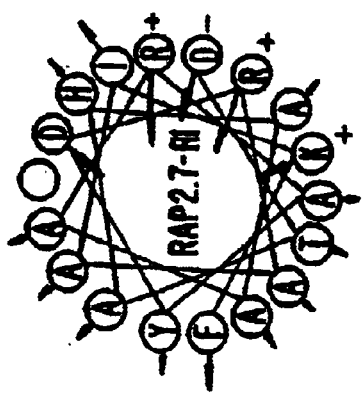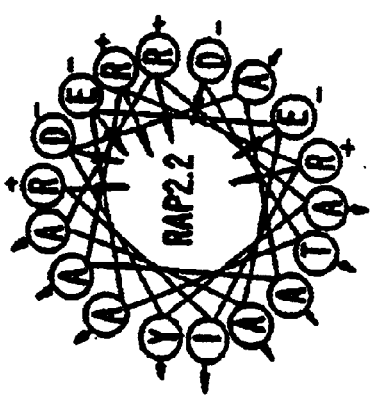
FIG. 4C. FIG. 4D.

METHODS FOR IMPROVING SEEDS

CROSS REFERENCE RELATED APPLICATIONS

This is a continuation-in-part of application U.S. Ser. No. 08/700,152, filed Aug. 20,1996, now U.S. Pat. No. 5,994,622, which is incorporated herein by reference.

FIELD OF THE INVENTION

The present invention is directed to plant genetic engineering. In particular, it relates to new methods for modulating mass and other properties of plant seeds.

BACKGROUND OF THE INVENTION

The pattern of flower development is controlled by the floral meristem, a complex tissue whose cells give rise to the different organ systems of the flower. Genetic and molecular studies have defined an evolutionarily conserved network of genes that control floral meristem identity and floral organ development in *Arabidopsis*, snapdragon, and other plant species (see, e.g., Coen and Carpenter, *Plant Cell* 5:1175–1181 (1993) and Okamuro et al., *Plant Cell* 5:1183–1193 (1993)). In *Arabidopsis*, a floral homeotic gene APETALA2 (AP2) controls three critical aspects of flower ontogeny—the establishment of the floral meristem (Irish and Sussex, *Plant Cell* 2:741–753 (1990); Huala and Sussex, *Plant Cell* 4:901–913 (1992); Bowman et al., *Development* 119:721–743 (1993); Schultz and Haughn, *Development* 119:745–765 (1993); Shannon and Meeks-Wagner, *Plant Cell* 5:639–655 (1993)), the specification of floral organ identity (Komaki et al., *Development* 104:195–203 (1988)); Bowman et al., *Plant Cell* 1:37–52 (1989); Kunst et al., *Plant Cell* 1:1195–1208 (1989)), and the temporal and spatial regulation of floral homeotic gene expression (Bowman et al., *Plant Cell* 3:749–758 (1991); Drews et al., *Cell* 65:91–1002 (1991)).

One early function of AP2 during flower development is to promote the establishment of the floral meristem. AP2 performs this function in cooperation with at least three other floral meristem genes, APETALA1 (AP1), LEAFY (LFY), and CAULIFLOWER (CAL) (Irish and Sussex (1990); Bowman, *Flowering Newsletter* 14:7–19 (1992); Huala and Sussex (1992); Bowman et al., (1993); Schultz and Haughn, (1993); Shannon and Meeks-Wagner, (1993)). A second function of AP2 is to regulate floral organ development. In *Arabidopsis*, the floral meristem produces four concentric rings or whorls of floral organs—sepals, petals, stamens, and carpels. In weak, partial loss-of-function ap2 mutants, sepals are homeotically transformed into leaves, and petals are transformed into pollen-producing stamenoid organs (Bowman et al., *Development* 112:1–20 (1991)). By contrast, in strong ap2 mutants, sepals are transformed into ovule-bearing carpels, petal development is suppressed, the number of stamens is reduced, and carpel fusion is often defective (Bowman et al., (1991)). Finally, the effects of ap2 on floral organ development are in part a result of a third function of AP2, which is to directly or indirectly regulate the expression of several flower-specific homeotic regulatory genes (Bowman et al., *Plant Cell* 3:749–758 (1991); Drews et al., *Cell* 65:91–1002 (1991); Jack et al. *Cell* 68:683–697 (1992); Mandel et al. *Cell* 71: 133–143 (1992)).

Clearly, Ap2 plays a critical role in the regulation of *Arabidopsis* flower development. Yet, little is known about how it carries out its functions at the cellular and molecular levels. A spatial and combinatorial model has been proposed to explain the role of AP2 and other floral homeotic genes in the specification of floral organ identity (see, e.g., Coen and Carpenter, supra). One central premise of this model is that AP2 and a second floral homeotic gene AGAMOUS (AG) are mutually antagonistic genes. That is, AP2 negatively regulates AG gene expression in sepals and petals, and conversely, AG negatively regulates AP2 gene expression in stamens and carpels. In situ hybridization analysis of AG gene expression in wild-type and ap2 mutant flowers has demonstrated that AP2 is indeed a negative regulator of AG expression. However, it is not yet known how AP2 controls AG. Nor is it known how AG influences AP2 gene activity.

The AP2 gene in *Arabidopsis* has been isolated by T-DNA insertional mutagenesis as described in Jofuku et al. *The Plant Cell* 6:1211–1225 (1994). AP2 encodes a putative nuclear factor that bears no significant similarity to any known fungal, or animal regulatory protein. Evidence provided there indicates that AP2 gene activity and function are not restricted to developing flowers, suggesting that it may play a broader role in the regulation of *Arabidopsis* development than originally proposed.

In spite of the recent progress in defining the genetic control of plant development, little progress has been reported in the identification and analysis of genes effecting agronomically important traits such as seed size, protein content, oil content and the like. Characterization of such genes would allow for the genetic engineering of plants with a variety of desirable traits. The present invention addresses these and other needs.

SUMMARY OF THE INVENTION

The present invention provides methods of modulating seed mass and other traits in plants. The methods involve providing a plant comprising a recombinant expression cassette containing an ADC nucleic acid linked to a plant promoter. The plant is either selfed or crossed with a second plant to produce a plurality of seeds. Seeds with the desired trait (e.g., altered mass) are then selected.

In some embodiments, transcription of the ADC nucleic acid inhibits expression of an endogenous ADC gene or activity the encoded protein. In these embodiments, the step of selecting includes the step of selecting seed with increased mass or another trait. The seed may have, for instance, increased protein content, carbohydrate content, or oil content. In the case of increased oil content, the types of fatty acids may or may not be altered as compared to the parental lines. In these embodiments, the ADC nucleic acid may be linked to the plant promoter in the sense or the antisense orientation. Alternatively, expression of the ADC nucleic acid may enhance expression of an endogenous ADC gene or ADC activity and the step of selecting includes the step of selecting seed with decreased mass. This embodiment is particularly useful for producing seedless varieties of crop plants.

If the first plant is crossed with a second plant the two plants may be the same or different species. The plants may be any higher plants, for example, members of the families Brassicaceae or Solanaceae. In making seed of the invention, either the female or the male parent plant can comprise the expression cassette containing the ADC nucleic acid. In preferred embodiments, both parents contain the expression cassette.

In the expression cassettes, the plant promoter may be a constitutive promoter, for example, the CaMV 35S promoter. Alternatively, the promoter may be a tissue specific promoter. Examples of tissue specific expression useful in the invention include fruit-specific, seed-specific (e.g., ovule-specific, embryo-specific, endosperm-specific, integument-specific, or seed coat-specific) expression.

The invention also provides seed produced by the methods described above. The seed of the invention comprise a recombinant expression cassette containing an ADC nucleic acid. If the expression cassette is used to inhibit expression of endogenous ADC expression, the seed will have a mass at least about 20% greater than the average mass of seeds of the same plant variety which lack the recombinant expression cassette. If the expression cassette is used to enhance expression of ADC, the seed will have a mass at least about 20% less than the average mass of seeds of the same plant variety which lack the recombinant expression cassette. Other traits such as protein content, carbohydrate content, and oil content can be altered in the same manner.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants. As defined here, a modified ADC coding sequence which is heterologous to an operably linked ADC promoter does not include the T-DNA insertional mutants (e.g., ap2–10) as described in Jofuku et al. *The Plant Cell* 6:1211–1225 (1994).

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

An "ADC (AP2 domain containing) nucleic acid" or "ADC polynucleotide sequence" of the invention is a subsequence or full length polynucleotide sequence of a gene which, encodes an polypeptide containing an AP2 domain and when present in a transgenic plant, can be used to modulate seed properties in seed produced by the plant. An exemplary nucleic acid of the invention is the *Arabidopsis* AP2 sequence as disclosed in Jofuku et al. *The Plant Cell* 6:1211–1225 (1994). The GenBank accession number for this sequence is U12546 (SEQ ID NO:3). As explained in detail below a family of RAP2 (related to AP2) genes have been identified in *Arabidopsis*. The class of nucleic acids claimed here falls into at least two subclasses (AP2-like and EREBP-like genes), which are distinguished by, for instance, the number of AP2 domains contained within each polypeptide and by sequences within certain conserved regions. The differences between these two subclasses are described in more detail below. ADC polynucleotides are defined by their ability to hybridize under defined conditions to the exemplified nucleic acids or PCR products derived from them. An ADC polynucleotide (e.g., AP2 or RAP2) is typically at least about 30–40 nucleotides to about 3000, usually less than about 5000 nucleotides in length. Usually the nucleic acids are from about 100 to about 2000 nucleotides, often from about 500 to about 1700 nucleotides in length.

ADC nucleic acids, as explained in more detail below, are a new class of plant regulatory genes that encode ADC polypeptides, which are distinguished by the presence of one or more of a 56–68 amino acid repeated motif, referred to here as the "AP2 domain". The amino acid sequence of an exemplary AP2 polypeptide is shown in Jofuku et al., supra. One of skill will recognize that in light of the present disclosure various modifications (e.g., substitutions, additions, and deletions) can be made to the sequences shown there without substantially affecting its function. These variations are specifically covered by the terms ADC polypeptide or ADC polynucleotide.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term ADC nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ADC nucleic acid", "AP2 nucleic acid" and "AP2 nucleic acid". In addition, the tern specifically includes those full length sequences substantially identical (determined as described below) with an ADC polynucleotide sequence and that encode proteins that retain the function of the ADC polypeptide (e.g., resulting from conservative substitutions of amino acids in the AP2 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 35%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, genomic DNA or cDNA comprising ADC nucleic acids of the invention can be identified in standard Southern blots under stringent conditions using the nucleic acid sequences disclosed here. For the purposes of this disclosure, stringent conditions for such hybridizations are those which include at least one wash in 0.2×SSC at a temperature of at least about 50° C., usually about 55° C. to about 60° C., for 20 minutes, or equivalent conditions. Other means by which nucleic acids of the invention can be identified are described in more detail below.

BRIEF DESCRIPTION OF THE DRAWINGS

FIGS. 4A and 4B show AP2 domain sequence and structure. The number of amino acid residues within each AP2 domain is shown to the right. Sequence gaps were introduced to maximize sequence alignments. The position of amino acid residues and sequence gaps within the AP2 domain alignments are numbered 1–77 for reference. The location of the conserved YRG (SEQ ID NO:1) and RAYD (SEQ ID NO:8) elements are indicated by brackets. Shaded boxes highlight regions of sequence similarity. Positively charged amino acids within the YRG element are indicated by + signs above the residues. The location of the 18-amino acid core region that is predicted to form an amphipathic α-helix in AP2 is indicated by a bracket. Residues within the RAYD (SEQ ID NO:8) element of each AP2 domain that are predicted to form an amphipathic α-helix are underlined. FIG. 4A shows members of the AP2-like subclass. Amino acid sequence alignment between the AP2 domain repeats R1 and R2 contained within AP2 (SEQ ID (NOs:4 and 5), ANT (SEQ ID NOs:9 and 10) and RAP2.7 (SEQ ID NOs:11 and 12) is shown. Brackets above the sequences designates the conserved YRG (SEQ ID NO:1) and RAYD (SEQ ID NO:8) blocks described above. The filled circle and asterisk indicate the positions of the ap2-1, and ap2-5 mutations, respectively. Amino acid residues that constitute a consensus AP2 domain motif for AP2, ANT, and RAP2.7 is shown below the alignment with invariant residues shown capitalized (SEQ ID NOs:13–16). FIG. 4B shows members of the EREBP-like subclass. Amino acid sequence Alignment between the AP2 domains contained within the tobacco EREBPs (SEQ ID NOs:17–20) and the *Arabidopsis* EREBP-like RAP2 proteins (SEQ ID NOs:21–31) is shown. Consensus sequences are shown as above (SEQ ID NOs: 32–35). GenBank accession numbers for EREBP-1, EREBP-2, EREBP-3, and EREBP-4 are D38123, D38126, D38124, and D38125, respectively.

FIG. 4C provides schematic diagrams of the putative RAP2.7-R1 (SEQ ID NO:36), AP2-R1 (SEQ ID NO:6), and ANT-R1 (SEQ ID NO:37) amphipathic α-helices. Amino acid residues within the RAP2.7-R1, AP2-R1, and ANT-R1 motifs shown underlined in A that are predicted to form amphipathic α-helices are schematically displayed with residues rotating clockwise by 100° per residue to form helical structures. Arrows directed toward or away from the center of the helical wheel diagrams indicate the negative or positive degree of hydrophobicity as defined by Jones et al. *J. Lipid Res.* 33:287–296 (1992). Positively and negatively charged amino acid residues are designated by + and − signs, respectively.

FIG. 4D shows schematic diagrams of the putative RAP2.2, RAP2.5, RAP2-12, and EREBP-3 amphipathic α-helices SEQ ID NOs:38, 40 and 41, repectively). Amino acid residues within the RAP2.2, RAP2.5, RAP2-12, and EREBP-3 motifs shown underlined in FIG. 4B that are predicted to form amphipathic α-helices are schematically displayed as described in FIG. 4C.

FIG. 4E shows sequence alignment between the 25–26 amino acid linker regions in AP2, ANT, and RAP2.7 (SEQ ID NOs: 42, 43 and 44, respectively). R1 and R2 designate the positions of the R1 and R2 repeats within AP2, ANT, and RAP2.7 relative to the linker region sequences. Boxes designate invariant residues within the conserved linker regions. Amino acid residues that constitute a consensus linker region motif for AP2, ANT, and RAP2.7 are shown below the alignment with invariant residues shown capitalized (SEQ ID NOs:45 and 46). The arrowhead indicates the position of the ant-3 mutation described by Klucher et al. *Plant Cell* 8:137–153 (1996).

DESCRIPTION OF THE PREFERRED EMBODIMENTS

Figures 1A, 1B:
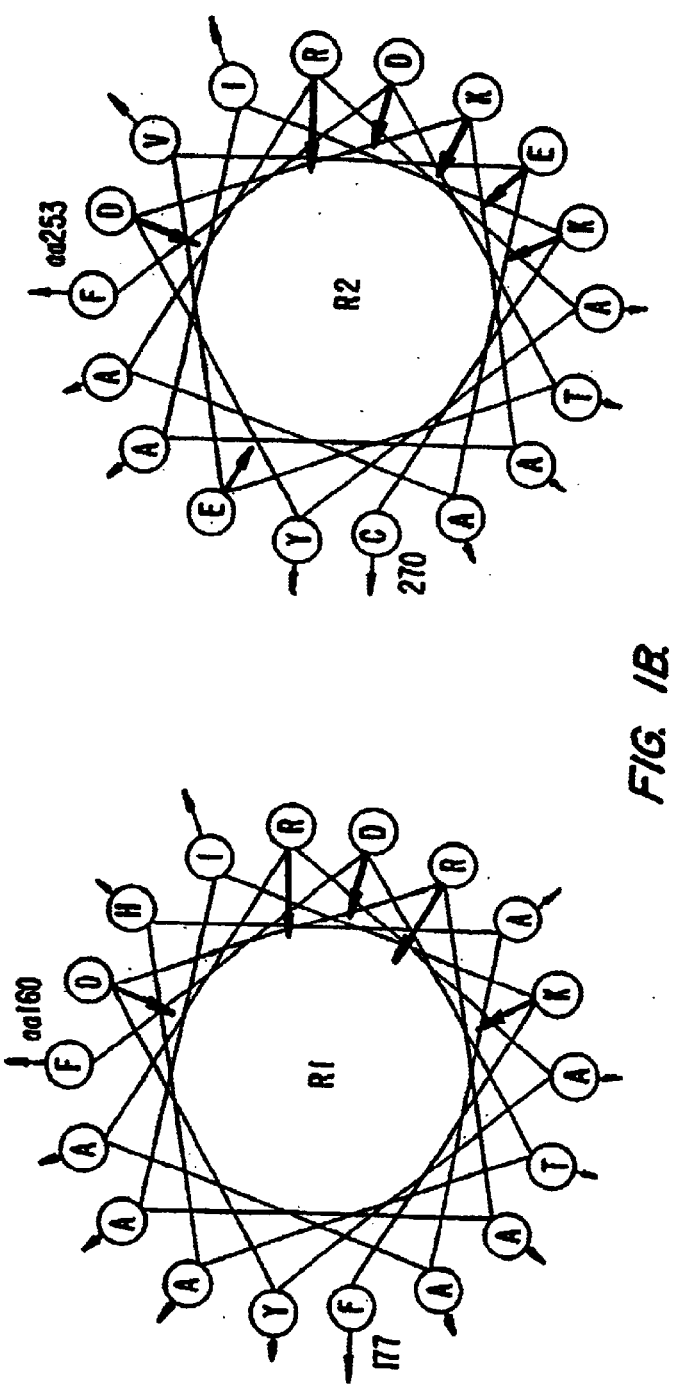
FIG. 1A shows amino acid sequence alignment between AP2 direct repeats AP2-R1 (aa 129–195 SEQ ID NO:4) and AP2-R2 (aa 221–28 SEQ ID NO:5). Solid and dashed lines between the two sequences indicate residue identity and similarity, respectively. Arrows indicate the positions of the ap2-1, ap2-5, and ap2-10 mutations described in Jofuku et al. (1994) The bracket above the AP2-R1 and AP2-R2 sequences indicates the residues capable of forming amphipathic α-helices shown in FIG. 1B.
FIG. 1B is a schematic diagram of the putative AP2-R1 (R1 SEQ ID NO:6) and AP2-R2 (R2 SEQ ID NO:7) amphipathic α-helices. The NH2 terminal ends of the R1 and R2 helices begin at residues Phe-160 and Phe-253 and rotate clockwise by 100° per residue through Phe-177 and Cys-270, respectively. Arrows directed toward or away from the center of the helical wheel diagrams indicate the negative or positive degree of hydrophobicity as defined by Jones et al. *J. Lipid Res.* 33: 87–296 (1992).

This invention relates to plant ADC genes, such as the AP2 and RAP2 genes of *Arabidopsis*. The invention provides molecular strategies for controlling seed size and total seed protein using ADC overexpression and antisense gene constructs. In particular, transgenic plants containing antisense constructs have dramatically increased seed mass, seed protein, or seed oil. Alternatively, overexpression of ADC using a constructs of the invention leads to reduced seed size and total seed protein. Together, data presented here demonstrate that a number of agronomically important traits including seed mass, total seed protein, and oil content, can be controlled in species of agricultural importance.

Isolation of ADC nucleic acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of ADC nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the ADC gene transcript is prepared from the in RNA. Alternatively, cDNA may be prepared from mRNA extracted from other tissues in which ADC genes or homologs are expressed.

The cDNA or genomic library can then be screened using a probe based upon the sequence of a cloned ADC gene disclosed here. Probes may be used to hybridize with genomic DNA or cDNA sequences to isolate homologous genes in the same or different plant species. Alternatively, antibodies raised against ADC can be used to screen an mRNA expression library.

Alternatively, the nucleic acids of interest can be amplified from nucleic acid samples using amplification techniques. For instance, polymerase chain reaction (PCR) technology to amplify the sequences of the ADC genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying ADC sequences from plant tissues are generated from comparisons of the sequences provided in Jofuku et al., supra. For a general overview of PCR see *PCR Protocols: A Guide to Methods and Applications*. (Innis, M, Gelfand, D., Sninsky, J. and White, T., eds.), Academic Press, San Diego (1990).

As noted above, the nucleic acids of the invention are characterized by the presence of sequence encoding a AP2 domain. Thus, these nucleic acids can be identified by their ability to specifically hybridize to sequences encoding AP2 domain disclosed here. Primers which specifically amplify AP2 domains of the exemplified genes are particularly useful for identification of particular ADC polynucleotides. Primers suitable for this purpose based on the sequence of RAP2 genes disclosed here are as follows:

| SEQ ID NO: | Name SEQ ID NO: 47 Through 62 | GenBank Number | Primers |
|---|---|---|---|
| 47 | AP2 | U12546 | JOAP2U 5'-GTTGCCGCTGCCGTAGTG-3' |
| 48 | | | JOAP2L 5'-GGTTCATCCTGAGCCGCATATC-3' |
| 49 | RAP2.1 | AF003094 | JORAP2.1U 5'-CTCAAGAAGAAGTGCCTAACCACG-3' |
| 50 | | | JORAP2.1L 5'-GCAGAAGCTAGAAGAGCGTCGA-3' |
| 51 | RAP2.2 | AF003095 | JORAP2.2U 5'-GGAAAATGGGCTGCGGAG-3' |
| 52 | | | JORAP2.2L 5'-GTTACCTCCAGCATCGAACGAG-3' |
| 53 | RAP2.4 | AF003097 | JORAP2.4U 5'-GCTGGATCTTGTTTCGCTTACG-3' |
| 54 | | | JORAP2.4L 5'-GCTTCAAGCTTAGCGTCGACTG-3' |
| 55 | RAP2.5 | AF003098 | JORAP2.5U 5'-AGATGGGCTTGAAACCCGAC-3' |
| 56 | | | JORAP2.5L 5'-CTGGCTAGGGCTACGCGC-3' |
| 57 | RAP2.6 | AF003099 | JORAP2.6U 5'-TTCTTTGCCTCCTCAACCATTG-3' |
| 58 | | | JORAP2.6L 5'-TCTGAGTTCCAACATTTTCGGG-3' |
| 59 | RAP2.7 | AF003100 | JORAP2.7U 5'-GAAATTGGTAACTCCGGTTCCG-3' |
| 60 | | | JORAP2.7L 5'-CCATTTTGCTTTGGCGCATTAC-3' |
| 61 | RAP2.8 | AF003101 | JORAP2.8U 5'-GGCGTTACGCCTCTACCGG-3' |
| 62 | | | JORAP2.8L 5'-CGCCGTCTTCCAGAACGTTC-3' |
| 63 | RAP2.9 | AF003102 | JORAP2.9U 5'-ATCACGGATCTGGCTTGGTTC-3' |
| 64 | | | JORAP2.9L 5'-GCCTTCTTCCGTATCAACGTCG-3' |
| 65 | RAP2.10 | AF003103 | JORAP2.10U 5'-GTCAACTCCGGCGGTTACG-3' |
| 66 | | | JORAP2.10L 5'-TCTCCTTATATACGCCGCCGA-3' |
| 67 | RAP2.11 | AP003104 | JORAP2.11U 5'-GAGAAGAGCAAAGGCAACAAGAC-3' |
| 68 | | | JORAP2.11L 5'-AGTTGTTAGGAAAATGGTTTGCG-3' |
| 69 | RAP2.12 | AF003105 | JORAP2.12U 5'-AAACCATTCGTTTTCACTTCGACTC-3' |
| 70 | | | JORAP2.12L 5'-TCACAGAGCGTTTCTGAGAATTAGC-3' |

The PCR primers are used under standard PCR conditions (described for instance in Innis et al.) using the nucleic acids as identified in the above GenBank accessions as a template. The PCR products generated by any of the reactions can then be used to identify nucleic acids of the invention (e.g., from a cDNA library) by their ability to hybridize to these products. Particularly preferred hybridization conditions use a Hybridization Buffer consisting of: 0.25M Phosphate Buffer (pH 7.2), 1 mM EDTA, 1% Bovine Serum Albumin, 7% SDS. Hybridizations then followed by a first wash with 2.0×SSC+0.1% SDS or 0.39M Na+ and subsequent washes with 0.2×SSC+0.1% SDS or 0.042M Na+. Hybridization temperature will be from about 45° C. to about 78° C., usually from about 50° C. to about 70° C. Followed by washes at 18° C.

Particularly preferred hybridization conditions are as follows:

| Hybridization Temp. | Hybrid. Time | Wash Buffer A | Wash Buffer B |
|---|---|---|---|
| 78 degrees C. | 48 hrs | 18 degrees C. | 18 degrees C. |
| 70 degrees C. | 48 hrs | 18 degrees C. | 18 degrees C. |
| 65 degrees C. | 48 hrs | 18 degrees C. | 18 degrees C. |
| 60 degrees C. | 72 hrs | 18 degrees C. | 18 degrees C. |
| 55 degrees C. | 96 hrs | 18 degrees C. | 18 degrees C. |
| 45 degrees C. | 200 hrs | 18 degrees C. | No wash |

If desired, primers that amplify regions are more specific to particular ADC genes can be used. The PCR products produced by these primers can be used in the hybridization conditions described above to isolate nucleic acids of the invention.

| SEQ ID NO: | Name SEQ ID NO: 71 Through 94 | GenBank Number | Primers |
|---|---|---|---|
| 71 | AP2 | U12546 | AP2U 5'-ATGTGGGATCTAAACGACGCAC-3' |
| 72 | | | AP2L 5'-GATCTTGGTCCACGCCGAC-3' |
| 73 | RAP2.1 | AF003094 | RAP2.1U 5'-AAG AGG ACC ATC TCT CAG-3' |
| 74 | | | RAP2.1L 5'-AAC ACT CGC TAG CTT CTC-3' |
| 75 | RAP2.2 | AF003095 | RAP2.2U 5'-TGG TTC AGC AGC CAA CAC-3' |
| 76 | | | RAP2.2L 5'-CAA TGC ATA GAG CTT GAG G-3' |
| 77 | RAP2.4 | AF003097 | RAP2.4U 5'-ACG GAT TTC ACA TCG GAG-3' |
| 78 | | | RAP2.4L 5'-CTA AGC TAG AAT CGA ATC C-3' |
| 79 | RAP2.5 | AF003098 | RAP2.5U 5'-TACCGGTTTCGCGCGTAG-3' |
| 80 | | | RAP2.5L 5'-CACCTTCGAAATCAACGACCG-3' |
| 81 | RAP2.6 | AF003099 | RAP2.6U 5'-TTCCCCGAAAATGTTGGAACTC-3' |
| 82 | | | RAP2.6L 5'-TGGGAGAGAAAAAATTGGTAGATCG-3' |
| 83 | RAP2.7 | AF003100 | RAP2.7U 5'-CGA TGG AGA CGA AGA CTC-3' |
| 84 | | | RAP2.7L 5'-GTC GGA ACC GGA GTT ACC-3' |
| 85 | RAP2.8 | AF003101 | RAP2.8U 5'-TCA CTC AAA GGC CGA GAT C-3' |
| 86 | | | RAP2.8L 5'-TAA CAA CAT CAC CGG CTC G-3' |
| 87 | RAP2.9 | AF003102 | RAP2.9U 5'-GTG AAG GCT TAG GAG GAG-3' |
| 88 | | | RAP2.9L 5'-TGC CTC ATA TGA GTC AGA G-3' |
| 89 | RAP2.10 | AF003103 | RAP2.10U 5'-TCCCGGAGCTTTTAGCCG-3' |
| 90 | | | RAP2.10L 5'-CAACCCGTTCCAACGATCC-3' |
| 91 | RAP2.11 | AF003104 | RAP2.11U 5'-TTCTTCACCAGAAGCAGAGCATG-3' |
| 92 | | | RAP2.11L 5'-CTCCATTCATTGCATATAGGGACG-3' |
| 93 | RAP2.12 | AF003105 | RAP2.12U 5'-GCTTTGGTTCAGAACTCGAACATC-3' |
| 94 | | | RAP2.12L 5'-AGGTTGATAAACGAACGATGCG-3' |

Polynucleotides may also be synthesized by well-known techniques as described in the technical literature. See, e.g., Carruthers et. al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Suppression of ADC activity or gene expression

One of skill will recognize that a number of methods can be used to inactivate or suppress ADC activity or gene expression. The control of the expression can be achieved by introducing mutations into the gene or using recombinant DNA techniques. These techniques are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Gene expression can be inactivated using recombinant DNA techniques by transforming plant cells with constricts comprising transposons or T-DNA sequences. ADC mutants prepared by these methods are identified according to standard techniques. For instance, mutants can be detected by PCR or by detecting the presence or absence of ADC mRNA, e.g., by Northern blots. Mutants can also be selected by assaying for increased seed mass, oil content and other properties.

The isolated sequences prepared as described herein, can also be used in a number of techniques to suppress endogenous ADC gene expression. A particularly useful genes for this purpose are the AP2 gene described in Jofuku et al., supra, and RAP2 genes described below.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805–8809 (1988), and Hiatt et al., U.S. Pat. No. 4,801,340.

The nucleic acid segment to be introduced generally will be substantially identical to at least a portion of the endogenous ADC gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of ADC genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. Nature, 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes see, Napoli et al., The Plant Cell 2:279–289 (1990), and U.S. Pat. Nos. 5,034,323, 5,231,020, and 5,283,184.

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Some ADC proteins (e.g., AP2) are believed to form multimers in vivo. As a result, an alternative method for inhibiting ADC function is through use of dominant negative mutants. This approach involves transformation of plants with constructs encoding mutant ADC polypeptides that form defective multimers with endogenous wild-type ADC proteins and thereby inactivate the protein. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate AG is described in Mizukami et al. Plant Cell 8:831–845 (1996).

Use of Nucleic Acids of the Invention to Enhance ADC Gene expression

Isolated sequences prepared as described herein can also be used to introduce expression of a particular ADC nucleic acid to enhance or increase endogenous gene expression. Enhanced expression will generally lead to smaller seeds or seedless fruit. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed. The distinguishing features of ADC polypeptides, including the AP2 domain, are discussed in detail below.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. Ann. Rev. Genet. 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumafaciens, and other transcription initiation regions from various plant genes known to those of skill. Such genes include for example, the AP2 gene, ACT11 from Arabidopsis (Huang et al. Plant Mol. Biol. 33:125–139 (1996)), Cat3 from Arabidopsis (GenBank No. U43147, Zhong et al., Mol. Gen. Genet. 251:196–203 (1996)), the gene encoding stearoyl-acyl carrier protein desaturase from Brassica napus. (Genbank No. X74782, Solocombe et al. Plant Physiol. 104:1167–1176 (1994)), GPc1 from maize (GenBank No. X15596, Martinez et al. J. Mol. Biol 208:551–565 (1989)), and Gpc2 from maize (GenBank No. U45855, Manjunath et al., Plant Mol. Biol. 33:97–112 (1997)).

Alternatively, the plant promoter may direct expression of the ADC nucleic acid in a specific tissue or may be otherwise under more precise environmental or developmental control. Such promoters are referred to here as "inducible" promoters. Examples of environmental conditions that may effect transcription by inducible promoters include anaerobic conditions, elevated temperature, or the presence of light.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific, embryo-specific, endosperm-specific, integument-specific, seed coat-specific, or some combination thereof. Examples include a promoter from the ovule-specific BEL1 gene described in Reiser et al. *Cell* 83:735–742 (1995) (GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mot. Biol.* 22:10131–1038 (1993), the gene encoding oleosin 18 kD from maize (GenBank No. J05212, Lee et al. *Plant Mol. Biol.* 26:1981–1987 (1994)), vivparous-1 from *Arabidopsis* (Genbank No. U93215), the gene encoding oleosin from *Arabidopsis* (Genbank No. Z17657), Atmyel from *Arabidopsis* (Urao et al. *Plant Mol. Biol.* 32:571–576 (1996), the 2s seed storage protein gene family from *Arabidopsis* (Conceicao et al. *Plant* 5:493–505 (1994)) the gene encoding oleosin 20 kD from *Brassica napus* (GenBank No. M63985), napA from *Brassica* napus (GenBank No. J02798, Josefsson et al. *JBL* 26: 12196–1301 (1987), the napin gene family from *Brassica napus* (Sjodahl et al. *Planta* 197:264–271 (1995), the gene encoding the 2S storage protein from *Brassica* napus (Dasgupta et al. *Gene* 133:301–302 (1993)), the genes encoding oleosin A (Genbank No. U09118) and oleosin B (Genbank No. U09119) from soybean and the gene encoding low molecular weight sulphur rich protein from in soybean (Choi et al. *Mol Gen, Genet.* 246:266–268 (1995)).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:7073 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture, pp.* 124–176, MacMillilan Publishing Company, New York, 1983; and Binding, *Regeneration of Plants, Plant Protoplasts, pp.* 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senccio, Sinapis, Solanum, Sorghum, Theobromus, Trigonella, Triticum, Vicia, Vitis, Vigna*, and *Zea*.

Increasing seed size, protein, amino acid, and oils content is particularly desirable in crop plants in which seed are used directly for animal or human consumption or for industrial purposes. Examples include soybean, canola, and grains such as rice, wheat, corn, rye, and the like. Decreasing seed size, or producing seedless varieties, is particularly important in plants grown for their fruit and in which large seeds may be undesirable. Examples include cucumbers, tomatoes, melons, and cherries.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Since transgenic expression of the nucleic acids of the invention leads to phenotypic changes in seeds and fruit, plants comprising the expression cassettes discussed above must be sexually crossed with a second plant to obtain the final product. The seed of the invention can be derived from a cross between two transgenic plants of the invention, or a cross between a plant of the invention and another plant. The desired effects (e.g., increased seed mass) are generally enhanced when both parental plants contain expression cassettes of the invention.

Seed obtained from plants of the present invention can be analyzed according to well known procedures to identify seed with the desired trait. Increased or decreased size can be determined by weighing seeds or by visual inspection. Protein content is conveniently measured by the method of Bradford et al *Anal. Bioch.* 72:248 (1976). Oil content is determined using standard procedures such as gas chromatography. These procedures can also be used to determine whether the types of fatty acids and other lipids are altered in the plants of the invention.

Using these procedures one of skill can identify the seed of the invention by the presence of the expression cassettes of the invention and increased seed mass. Usually, the seed mass will be at least about 10%, often about 20% greater than the average seed mass of plants of the same variety that lack the expression cassette. The mass can be about 50% greater and preferably at least about 75% to about 100% greater. Increases in other properties e.g., protein and oil will usually be proportional to the increases in mass. Thus, in some embodiments protein or oil content can increase by about 10%, 20%, 50%, 75% or 100%, or in approximate proportion to the increase in mass.

Alternatively, seed of the invention in which AP2 expression is enhanced will have the expression cassettes of the invention and decreased seed mass. Seed mass will be at least about 20% less than the average seed mass of plants of the same variety that lack the expression cassette. Often the mass will be about 50% less and preferably at least about 75% less or the seed will be absent. As above, decreases in other properties e.g., protein and oil will be proportional to the decreases in mass.

The following Examples are offered by way of illustration, not limitation.

EXAMPLE 1

AP2 Gene Isolation

The isolation and characterization of an AP2 gene from *Arobidopsis* is described in detail in Jofuku el at., supra. Briefly, T-DNA from *Agrobacterium* was used as an insertional mutagen to identify and isolate genes controlling flower formation in *Arabidopsis*. One transformed line, designated T10, segregated 3 to 1 for a flower mutant that phenotypically resembled many allelic forms of the floral homeotic mutant ap2. T10 was tested and it was confirmed genetically that T10 and ap2 are allelic. The mutant was designated as ap2-10.

It was determined that ap2-10 was the product of a T-DNA insertion mutation by genetic linkage analysis using the T-DNA-encoded neomycin phosphotransferase II (NPTII) gene as a genetic marker. An overlapping set of T-DNA-containing recombinant phage was selected from an ap2-10 genome library and the plant DNA sequences flanking the T-DNA insertion element were used as hybridization probes to isolate phage containing the corresponding region from a wild-type *Arabidopsis* genome library. The site of T-DNA insertion in ap2-10 was mapped to a 7.2-kb EcoR1 fragment centrally located within the AP2 gene region.

Five *Arabidopsis* flower cDNA clones corresponding to sequences within the 7.2-kb AP2 gene region were isolated. All five cloned cDNAs were confirmed to represent AP2 gene transcripts using an antisense gene strategy to induce ap2 mutant flowers in wild-type plants.

To determine AP2 gene structure, the nucleotide sequences of the cDNA inserts were compared to that of the 7.2-kb AP2 genomic fragment. These results showed that the AP2 gene is 2.5 kb in length and contains 10 exons and 9 introns that range from 85 to 110 bp in length. The AP2 gene encodes a theoretical polypeptide of 432 amino acids with a predicted molecular mass of 48 kD. The A P2 nucleotide and predicted protein sequences were compared with a merged, nonredundant data base. It was found that AP2 had no significant global similarity to any known regulatory protein.

Sequence analysis, however, did reveal the presence of several sequence features that may be important for AP2 protein structure or function. First, AP2 contains a 37-amino acid serine-rich acidic domain (amino acids 14 to 50) that is analogous to regions that function as activation domains in a number of RNA polymerase II transcription factors. Second, AP2 has a highly basic 10-amino acid domain (amino acids 119 to 128) that includes a putative nuclear localization sequence KKSR (SEQ ID NO:95) suggest that AP2 may function in the nucleus. Finally, that the central core of the AP2 polypeptide (amino acids 129 to 288) contains two copies of a 68-amino acid direct repeat that is referred to here as the AP2 domain. The two copies of this repeat, designated AP2-RJ and AP2-R2, share 53% amino acid identity and 69% amino acid homology. FIG. 1A shows that each AP2 repeat contains an 18-amino acid conserved core region that shares 83% amino acid homology. FIG. 1B shows that both copies of this core region are theoretically capable of forming amphipathic α-helical structures that may participate in protein-protein interactions.

EXAMPLE 2

Preparation of A P2 Constructs

Figure 2:
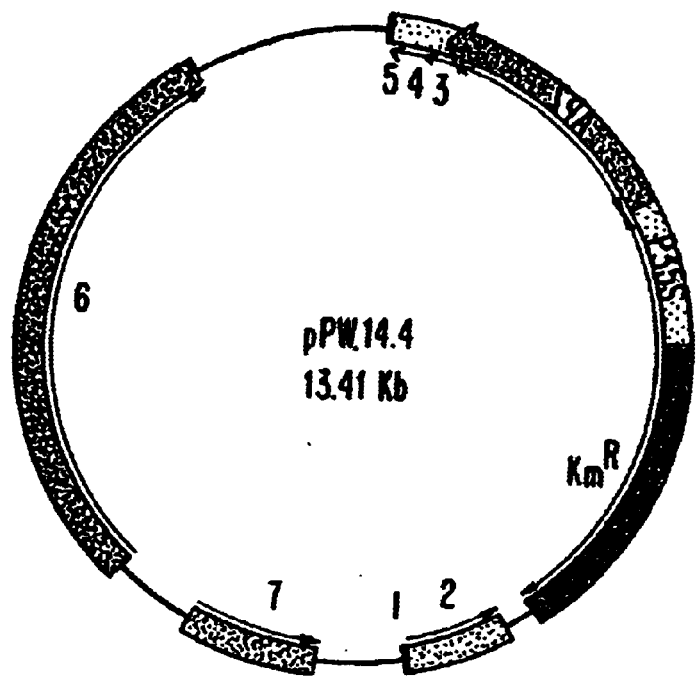
FIG. 2 shows an antisense construct of the invention. pPW140.4 (which is identical to pPW15) represents the 13.41 kb AP2 antisense gene construct used in plant transformation described here. pPW140.4 is comprised of the AP2 gene coding region in a transcriptional fusion with the cauliflower mosaic virus 35S (P35S) constitutive promoter in an antisense orientation. The Ti plasmid vector used is a modified version of the pGSJ780A vector (Plant Genetic Systems, Gent, Belgium) in which a unique EcoR1 restriction site was introduced into the BamH1 site using a Cla1-EcoR1-BamH1 adaptor. The modified pGSJ780A vector DNA was linearized with EcoR1 and the AP2 coding region inserted as a 1.68 kb EcoR1 DNA fragment from AP2 cDNA plasmid cAP2#1 (Jofuku et al., 1994) in an antisense orientation with respect to the 35S promoter. KmR represents the plant selectable marker gene NPTII which confers resistance to the antibiotic kanamycin to transformed plant cells carrying an integrated 35S-AP2 antisense gene. Boxes 1 and 5 represent the T-DNA left and right border sequences, respectively, that are required for transfer of T-DNA containing the 35S-AP2 antisense gene construct into the plant genome. Regions 2 and 3 contain T-DNA sequences. Box 3 designates the 3' octopine synthase gene sequences that function in transcriptional termination. Region 6 designates bacterial DNA sequences that function as a bacterial origin of replication in both *E. coli* and *Agrobacterium tumefaciens*, thus allowing pPW14.4 plasmid replication and retention in both bacteria. Box 7 represents the bacterial selectable marker gene that confers resistance to the antibiotics streptomycin and spectinomycin and allows for selection of *Agrobacterium* strains that carry the pPW14.4 recombinant plasmid.
Figure 3:
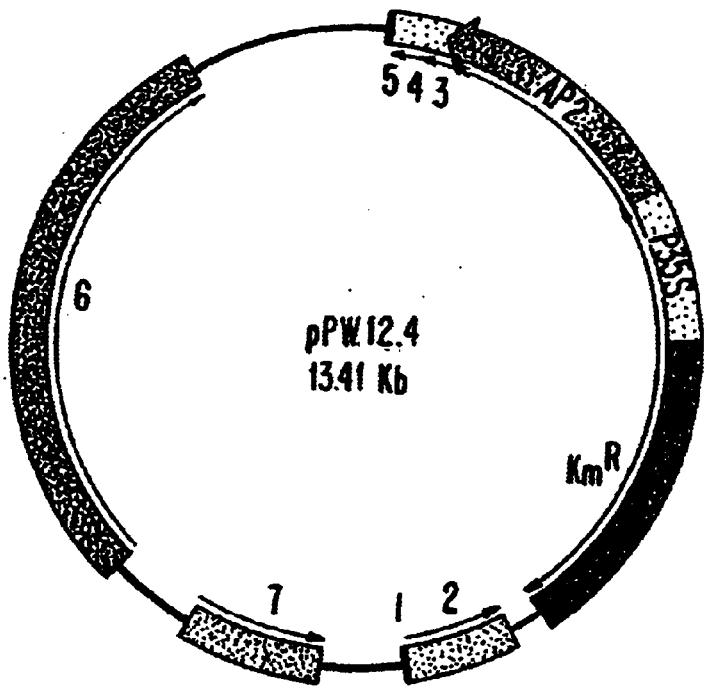
FIG. 3 shows a sense construct of the invention. pPW12.4 (which is identical to pPW9) represents the 13.41 kb AP2 sense gene construct used in plant transformation described here. pPW12.4 is comprised of the AP2 gene coding region in a transcriptional fusion with the cauliflower mosaic virus 35S(P35S) constitutive promoter in a sense orientation. The Ti plasmid vector used is a modified version of the pGSJ780A vector (Plant Genetic Systems, Gent, Belgium) in which a unique EcoR1 restriction site was introduced into the BamH1 site using a Cla1-EcoR1-BamH1 adaptor. The modified pGSJ780A vector DNA was linearized with EcoR1 and the AP2 coding region inserted as a 1.68 kb EcoR1 DNA fragment from AP2 cDNA plasmid cAP2#1 (Jofuku et al., 1994) in a sense orientation with respect to the 35S promoter. KmR represents the plant selectable marker gene NPTII which confers resistance to the antibiotic kanamycin to transformed plant cells carrying an integrated 35S-AP2 antisense gene. Boxes 1 and 5 represent the T-DNA left and right border sequences, respectively, that are required for transfer of T-DNA containing the 35S-AP2 sense gene constrict into the plant genome. Regions 2 and 3 contain T-DNA sequences. Box 3 designates the 3' octopine synthase gene sequences that function in transcriptional termination. Region 6 designates bacterial DNA sequences that function as a bacterial origin of replication in both *E. coli* and *Agrobacterium tumefaciens*, thus allowing pPW12.4 plasmid replication and retention in both bacteria. Box 7 represents the bacterial selectable marker gene that confers resistance to the antibiotics streptomycin and spectinomycin and allows for selection of *Agrobacterium* strains that carry the pPW12.4 recombinant plasmid.

Gene constructs were made comprising the AP2 gene coding region described above in a transcriptional fusion with the cauliflower mosaic virus 35S constitutive promoter in both the sense and antisense orientations. The original vector containing the 35S promoter pGSJ780A was obtained from Plant Genetic Systems (Gent, Belgium). The pGSJ780A vector was modified by inserting a Cla1-BamH1 adaptor containing an EcoR1 site in the unique BamH1 site of pGSJ780A. The modified pGSJ780A DNA was linearized with EcoR1 and the AP2 gene coding region inserted as a 1.68 kb EcoR1 fragment in both sense and antisense orientations with respect to the 35S promoter (see, FIGS. 2 and 3).

The resultant DNA was transformed into *E. coli* and spectinomycin resistant transformants were selected. Plasmid DNAs were isolated from individual transformants and the orientation of the insert DNAs relative to the 35S promoter were confirmed by DNA sequencing. Bacterial cells containing the 35S/AP2 sense (designated pPW12.4 and pPW9) and 35S/AP2 antisense (designated pPW14.4 and pPW15) constructs were conjugated to *Agrobacterium tumefaciens* and rifampicin, spectinomycin resistant transformants were selected for use in *Agrobacterium*-mediated plant transformation experiments.

The 35S/AP2 sense and 35I/AP2 antisense constructs were introduced into wild-type *Arabidopsis* and tobacco plants according to standard techniques. Stable transgenic plant lines were selected using the plant selectable marker NPTII (which confers resistance to the antibiotic kanamycin) present on the modified Ti plasmid vector pGSJ780A.

EXAMPLE 3

Modification of Seed using AP2 Sequences

This example shows that ap2 mutant plants and transgenic plants containing the 35S/AP2 antisense construct produced seed with increased mass and total protein content. By contrast, transgenic plants containing the 35S/AP2 sense construct produced seed with decreased mass and protein content. Together these results indicate that seed mass and seed contents in transgenic plants can be modified by genetically altering AP2 activity.

Seed from 30 lines were analyzed for altered seed size and seed protein content including the *Arabidopsis* ap2 mutants ap2-1, ap2-3, ap2-4, ap2-5, ap2-6, ap2-9 and ap2-10 and transgenic *Arabidopsis* and transgenic tobacco containing the CaMV 35S/AP2 antisense gene construct, the CaMV 35S/AP2 sense gene construct, or the pGSJ780A vector as described above. The ap2 mutants used in this study are described in Komaki et al., *Development* 104, 195–203 (1988), Kunst et ol., *Plant Cell* 1, 1195–1208 (1989), Bowman et al., *Development* 112, 1–20 (1991), and Jofuku et al., supra.

Due to the small size of *Arabidopsis* and tobacco seed, average seed mass was determined by weighing seed in batches of 100 for *Arabidopsis* and 50 seed for tobacco. The net change in seed mass due to changes in AP2 gene activity was calculated by subtracting the average mass of wild-type seed from mutant seed mass.

Seed from three wild-type *Arabidopsis* ecotypes C24, Landsberg-er, and Columbia, and one wild-type tobacco SR1 were used as controls. Wild-type *Arabidopsis* seed display seasonal variations in seed mass which range from 1.6–2.3 mg per 100 seed as shown in Table I. Therefore transgenic *Arabidopsis* seed were compared to control seed that had been harvested at approximately the same time of season. This proved to be an important for comparing the effects of weak ap2 mutations on seed mass.

Table I shows that all ap2 mutant seed examined, ap2-1, ap2-3, ap2-4, ap2-5, ap2-6, ap2-9, and ap2-10, show a significant increase in average seed mass ranging from +27 to +104 percent compared to wild-type. The weak partial loss-of-function mutants such as ap2-1 and ap2-3 show the smallest gain in average seed mass ranging from +27 percent to +40 percent of wild-type, respectively. By contrast, strong ap2 mutants such as ap2-6 and ap2-10 show the largest gain in seed mass ranging from +69 percent to +104 percent of wild-type, respectively. Thus reducing AP2 gene activity genetically consistently increases *Arabidopsis* seed mass.

AP2 antisense and AP2 sense cosuppression strategies described above were used to reduce AP2 gene activity in planta to determine whether seed mass could be manipulated in transgenic wild-type plants. Twenty-nine independent lines of transgenic *Arabidopsis* containing the CaMV 35S/AP2 antisense gene constructs pPW14.4 and pPW15 (FIG. 2) were generated. Each transgenic line used in this study tested positive for kanamycin resistance and the presence of one or more copies of T-DNA.

Table I shows that seed from nine transgenic *Arabidopsis* AP2 antisense lines show a significant increase in seed mass when compared to control seed ranging from +22 percent for line C24 15-542 to +89 percent for line C24 15-566. Both C24 and Landsberg-er ecotypes were used successfully. Increased seed mass was observed in F1, F2, and F3 generation seed.

Eight lines containing the 35S/AP2 sense gene construct were generated which were phenotypically cosuppression mutants. As shown in Table I seed from two cosuppression lines examined showed larger seed that range from +26 percent to +86 percent. By contrast, plants transformed with the vector pGSJ780A showed a normal range of average seed mass ranging from −0.5 percent to +13 percent compared to wild-type seed (Table I). Together, these results demonstrate that AP2 gene sequences can be used to produce a significant increase in *Arabidopsis* seed mass using both antisense and cosuppression strategies in a flowering plant.

TABLE I

Genetic control of Arabidopsis seed mass by AP2.

| | Average seed mass in mg per 100 seed[1,2] | Percent change in seed mass compared to wild-type |
|---|---|---|
| ap2 mutant seed | 2.1 (0.1) | +27% |
| 1. ap2-1 | 2.2 (0.1) | +33% |
| | 2.1 (0.2) | +31% |
| | 2.8 (0.2) | +33% |
| 2. ap2-3 | 2.6 (0.1) | +27% |
| 3. ap2-4 | 3.5 (0.3) | +69% |
| | 3.5 (0.2) | +69% |
| 4. ap2-5 | 2.9 (0.1) | +39% |
| 5. ap2-6 | 3.5 (0.2) | +69% |
| 6. ap2-9 | 2.9 (0.1) | +49% |
| 7. ap2-10 | 3.7 (0.4) | +79% |
| | 3.9 (0.3) | +90% |
| | 4.2 (0.5) | +104% |
| Seed produced by transgenic CaMV35S/AP2 antisense lines (from a Km resistant mother) | | |
| 1. C24 14.4E (F1-15) F2 sd | 3.1 | +35% |
| C24 14.4E (F1-15) F3 sd | 3.4 (0.3) | +47% |
| 2. C24 14.4S (F1-1) | 2.8 (0.2) | +29% |
| 3. C24 14.4AA (F1-24) | 2.9 (0.1) | +30% |
| 4. C24 14.4DD (F1-2) | 2.8 (0.3) | +30% |
| 5. C24 15-522 | 3.6 (0.1) | +76% |
| 6. C24 15-542 (F1-2) | 2.6 (0.1) | +25% |
| C24 15-542 (F1-7) | 2.5 (0.2) | +22% |
| 7. C24 15-566 | 3.9 (0.1) | +89% |
| 8. LE 15-9992-3 (F1-1) F2 sd | 2.4 (0.1) | +42% |
| 9. LE 15-83192-3 (F1-3) | 2.8 (0.0) | +33% |
| LE 15-83192-3 (F1-17) | 2.7 (0.0) | +28% |
| Seed produced by transgenic CaMV35S/AP2 cosuppression lines (from a Km resistant mother) | | |
| 1. C24 9-5 (F1-5) | 3.8 (0.0) | +86% |
| 2. LE 9-83192-2 (F1-19) | 2.7 (0.2) | +26% |
| LE 9-83192-2 (F1-24) | 2.7 (0.1) | +26% |
| Seed produced by transgenic pGSJ780A vector only lines (from a Km resistant mother plant) | | |
| 1. C24 3-107 (F1-1) | 2.2 (0.1) | +9% |
| 2. C24 3-109 (F1-1) | 2.3 (0.0) | +13% |
| 3. LE 3-83192-1 (F1-2) | 2.3 (0.1) | +7% |
| 4. LE 3-83192-3 (F1-2) | 2.4 (0.1) | +11% |
| 5. LE 3-9992-4 (F1-4) | 2.4 (0.2) | +12% |
| LE 3-9992-4 (F1-6) | 2.3 (0.0) | +9% |
| LE 3-9992-4 (F1-8) | 2.1 (0.0) | −0.5% |
| 6. LE 3-9992-9 (F1-3) | 2.3 (0.1) | +7% |
| Seed produced by wild-type Arabidopsis plants | | |
| 1. C24 | 2.0 (0.1) | |
| | 2.3 (0.1) | |
| | 2.2 | |
| 2. Landsberg-er | 1.6 (0.1) | |
| | 2.1 (0.1) | |
| | 2.1 | |
| | 2.3 (0.1) | |
| 3. Columbia | 1.8 (0.1) | |
| | 2.1 (0.1) | |

[1]Standard deviation values are given in parentheses.
[2]Wild-type seed values used for this comparison were chosen by ecotype and harvest date.

Arabidopsis AP2 gene sequences were also used to negatively control seed mass in tobacco, a heterologous plant species. Table II shows that in five transgenic tobacco lines the CaMV 35S/AP2 overexpression gene construct was effective in reducing transgenic seed mass from −27 percent to −38 percent compared to wild-type seed. These results demonstrate the evolutionary conservation of AP2 gene function at the protein level for controlling seed mass in a heterologous system.

TABLE II

Genetic control of tobacco seed mass using Arabidopsis AP2.

| | Average seed mass in mg per 5 seed[1] | Percent change in seed mass compared to wild-type |
|---|---|---|
| 1. SR1 9-110 To | 3.1 (0.0) | −27% |
| SR1 9-110 (F1-5) | 3.0 (0.2) | −29% |
| | 2.8 (0.3) | −34% |
| 2. SR1 9-202 (F1-G) | 3.1 (0.2) | −27% |
| SR1 9-202 (F1-1) | 3.2 (0.1) | −24% |
| 3. SR1 9-103 (F1-2) | 3.9 (0.0) | −8% |
| 4. SR1 9-413-1 | 2.8 (0.0) | −34% |
| | 3.0 (0.2) | −29% |
| 5. SR1 9-418-1 To | 3.5 (0.1) | −18% |
| Seed produced by transgenic CaMV 35S/AP2 antisense gene lines (from a Km resistant mother) | | |
| 1. SR1 15-111 | 5.1 (0.4) | +20% |
| SR1 15-111 (F1) | 5.0 (0.4) | +19% |
| 2. SR1 15-116 To | 4.1 (0.4) | −3% |
| SR1 15-116 (F1-2) | 4.0 (0.1) | −5% |
| SR1 15-116 (F1-1) | 4.5 (0.1) | +5% |
| 3. SR1 15-407 (F1) | 4.8 (0.5) | +10% |
| | 4.7 (0.3) | +10% |
| 4. SR1 15-102 (F1) | 4.5 (0.2) | +6% |
| 5. SR1 15-413 (F1-3) | 4.2 (0.0) | +0% |
| 6. SR1 15-410 (F1-2) | 4.4 (0.0) | +4% |
| 7. SR1 15-210 (F1-4) | 3.6 (0.1) | −15% |
| Seed produced by pGSJ780A vector only lines (from a Km resistant mother) | | |
| 1. SR1 3-402 (F1) | 5.0 (0.1) | +17% |
| 2. SR1 3-401 (F1) | 4.6 (0.1) | +8% |
| 3. SR1 3-405 (F1) | 4.4 (0.1) | +4% |
| Seed from wild-type tobacco | | |
| 1. SR1 | 4.2 (0.3) | |
| | 4.0 (0.1) | |

[1]Standard deviation values are given in parentheses.

Use of AP2 Gene Constructs to Control Seed Protein Content

Total seed protein was extracted and quantitated from seed produced by wild-type, ap2 mutant, transgenic AP2 antisense, and transgenic AP2 sense cosuppression plants according to Naito et al. *Plant Mol. Biol.* 11, 109–123 (1988). Seed protein was extracted in triplicate from batches of 100 dried seed for *Arabidopsis* or 50 dried seed for tobacco. Total protein yield was determined by the Bradford dye-binding procedure as described by Bradford, *Anal. Biochem.* 72:248 (1976). The results of this analysis are shown in Table III.

ap2 mutant total seed protein content increased by 20 percent to 78 percent compared to wild-type control seed. Total seed protein from transgenic AP2 antisense plants increased by +31 percent to +97 percent compared to wild-type controls. Transgenic AP2 cosuppression seed showed a +13 and +17 percent increase over wild-type. Together, the transgenic antisense and cosuppression mutant seed consistently yielded more protein per seed than did the wild-type controls or transgenic plants containing the pGSJ780A vector only (Table III).

| | Total seed protein in μg per 100 seed[1] | Percent change in protein content compared to wild-type |
|---|---|---|
| ap2 mutant seed | | |
| 1. ap2-1 | 652 (17) | +20% relative to WT seed |
| | 615 (30) | +11% |
| 2. ap2-3 | 705 (47) | +27% |
| 3. ap2-4 | 729 (107) | +33% |
| 4. ap2-5 | 617 (24) | +13% |
| 5. ap2-6 | 836 (14) | +52% |
| 6. ap2-9 | 798 (11) | +46% |
| 7. ap2-10 | 536 (15) | +78% |
| Transgenic CaMV 35S/AP2 antisense see mass (from Km resistant mother) | | |
| 1. C24 14.4E (F1-1) F3 sd | 615 (60) | +31% |
| 2. C24 15-522 (F1-1) | 790 (23) | +68% |
| 3. C24 15-566 | 925 (173) | +97% |
| Transgenic CaMV 35S/AP2 sense cosuppression seed mass (from Km Resistant mother plant) | | |
| 1. LE 9-83192-2 (F1-19) | 616 | +13% |
| LE 9-83192-2 (F1-24) | 637 | +17% |
| Wild-type seed | | |
| 1. C24 | 469 (19) | |
| 2. LE | 545 (22) | |
| | 555 | |
| 3. Col | 548 (42) | |

[1]Standard deviation values are given in parentheses.

Transgenic tobacco containing the 35S/AP2 sense gene construct show that AP2 overexpression can decrease seed protein content by 27 to 45 percent compared to wild-type seed. Together, the transgenic *Arabidopsis* and tobacco results demonstrate that seed mass and seed protein production can be controlled by regulating AP2 gene activity.

TABLE IV

Negative control of transgenic tobacco seed protein content by Arabidopsis AP2 gene expression.[1]

| | Ave. protein per 50 seed | Percent change in protein content compared to wild-type |
|---|---|---|
| Seed produced by transgenic CAMV 35S/AP2 sense gene plant. | | |
| 1. SR1 9-110 | 242 (11) | −45% |
| 2. SR1 9-202 (F1-G) | 271 (11) | −38% |
| 3. SR1 9-413 | 362 (8) | −18% |
| 4. SR1 9-418-1 | 319 (16) | −27% |
| Wild-type Control | | |
| SR1 (wild-type) | 440 (8) (JO) | NA |

[1]Standard deviation values are given in parentheses.

Analysis of Transgenic Seed Proteins by Gel Electrophoresis

*Arabidopsis* seed produce two major classes of seed storage proteins, the 12S cruciferins and 2S napins which are structurally related to the major storage proteins found in the *Brassicaceae* and in the *Leguminoceae*. The composition of seed proteins in wild-type, ap2 mutant, and transgenic *Arabidopsis* seed were compared by SDS polyacrylamide gel electrophoresis as described by Naito et al., *Plant Mol. Biol.* 11, 109–123 (1988). Total seed proteins were extracted as described above. 50 μg aliquots were separated by gel electrophoresis and stained using Coomassie brilliant blue. These results showed that the spectrum of proteins in wild-type and ap2 mutant seed are qualitatively indistinguishable. There is no detectable difference in the representation of the 12S or 2S storage proteins between the wild-type and ap2 mutant seed extracts. This shows that reducing AP2 gene activity genetically does not alter the profile of storage proteins synthesized during seed maturation. The spectrum of seed proteins produced in transgenic AP2 antisense and AP2 sense cosuppression seed are also indistinguishable from wild-type. In particular, there is no detectable difference in the representation of the 12S cruciferin or 2S napin storage proteins in the larger seed.

Finally, the transgenic tobacco plants containing the 35S/AP2 overexpression gene construct produced significantly smaller seed. Despite the decrease in seed mass in transgenic tobacco there was no detectable difference in storage protein profiles between seed from 35S/AP2 transformants and wild-type SR1.

EXAMPLE 4

Isolation of Other Members of the AP2 Gene Family from *Arabidopsis*

This example describes isolation of a number of AP2 nucleic acids from *Arabidopsis*. The nucleic acids are referred to here as RAP2 (related to AP2) were identified using primers specific to nucleic acid sequences from the AP2 domain described above.

Materials and Methods

Plant Material. *Arabidopsis thaliana* ecotype Landsberg erecta (L-er) and C24 were used as wild type. Plants were grown at 22° C. under a 16-hr light/8-hr dark photoperiod in a 1:1:1 mixture containing vermiculite/perlite/peat moss. Plants were watered with a one-fourth strength Peter's solution (Grace-Sierra, Milpitas, Calif.). Root tissue was harvested from plants grown hydroponically in sterile flasks containing 1×Murashige and Skoog plant salts (GIBCO), 1 mg/liter thiamine, 0.5 mg/liter pyridoxine, 0.5 mg/liter nicotinic acid, 0.5 g/liter 2-(N-morpholino)ethanesulfonic acid (MES), and 3% sucrose, with moderate shaking and 70 $\mu$mol-m$^{-2}$-sec$^{-1}$ of light.

Analysis of cloned *Arabidopsis* cDNAs. *Arabidopsis* expressed sequence tagged (EST) CDNA clones representing RAP2.1 and RAP2.9 were generated as described by Cooke et al. (Cooke, R., et al., 1996, *Plant J.* 9, 101–124). EST cDNA clones representing RAP2.2 and RAP2.8 were generated as described by Höfte et al. (Höfte, H., et al., 1993, *Plant J.* 4, 1051–1061). EST cDNA clones representing all other RAP2 genes were generated by Newman et al. (Newman, T., et al., 1994, *Plant Physiol.* 106,1241–1255) and provided by the *Arabidopsis* Biological Resource Center (Ohio State University). Plasmid DNAs were isolated and purified by anion exchange chromatography (Qiagen, Chatsworth, Calif.). DNA sequences were generated using fluorescence dye-based nucleotide terminators and analyzed as specified by the manufacturer (Applied Biosystems).

Nucleotide and Amino Acid Sequence Comparisons. The TBLASTN program (Altschul, S. F., et al., 1990, *J. Mol. Biol.* 215, 403–410) and default parameter settings were used to search the *Arabidopsis* EST database (AAtDB 4–7) for genes that encode AP2 domain-containing proteins. Amino acid sequence alignments were generated using the CLUSTAL W multiple sequence alignment program (Thompson, J. D., et al., 1994, *Nucleic Acids Res.* 22, 4673–4680). Secondary structure predictions were based on the principles and software programs described by Rost (Rost, B., 1996, *Methods Enzymol.* 266, 525–539) and Rost and Sander (Rost, B., et at, 1993, *J. Mol. Biol.* 232, 589–599; Rost, B., et al., 1994, *Proteins* 19, 55–77).

RAP2 Gene-Specific Probes. RAP2 gene-specific fragments were generated by PCR using gene-specific primers and individual RAP2 plasmid DNAs as a template as specified by Perkin-Elmer (Roche Molecular Systems, Branchburg, N.J.). The following primers were used to generate fragments representing each RAP2 gene:

RAP2.1 (SEQ ID NOs:73 and 74 respectively), 5'-AAGAGGACCATCTCTCAG-3', 5'-AACACTCGCTAGCTTCTC-3';
RAP2.2 (SEQ ID NOs:75 and 76, respectively), 5'-TGGTTCAGCAGCCAACAC-3', 5'-CAATGCATAGAGCTTGAGG-3';
RAP2.3 (SEQ ID NOs:96 and 97, respectively), 5'-TCATCGCCACGATCAACC-3', 5'-AGCAGTCCAATGCGACGG-3';
RAP2.4 (SEQ ID NOs:77 and 78, respectively), 5'-ACGGATTTCACATCGGAG-3', 5'-CTAAGCTAGAATCGAATCC-3';
RAP2.7 (SEQ ID NOs:83 and 84, respectively), 5'-CGATGGAGACGAAGACTC-3', 5'-GTCGGAACCGGAGTTACC-3';
RAP2.8 (SEQ ID NOs:85 and 86, respectively), 5'-TCACTCAAAGGCCGAGATC-3', 5'-TAACAACATCACCGGCTCG-3';
RAP2.9 (SEQ ID NOs: 87 and 88 respectively) 5'-GTGAAGGCTTAGGAGGAG-3', 5'-TGCCTCATATGAGTCAGAG-3'.

PCR-synthesized DNA fragments were gel purified and radioactively labeled using random oligonucleotides (Amersham) for use as probes in gene mapping and RNA gel blot experiments.

Gene Mapping Experiments. RAP2 genes were placed on the *Arabidopsis* genetic map by either restriction fragment length polymorphism segregation analysis using recombinant inbred lines as described by Reiter et al. (Reiter, R. S., et al., 1992, *Proc. Natl. Acad. Sci. USA* 89, 1477–1481) or by matrix-based analysis of pooled DNAs from the *Arabidopsis* yUP or CIC yeast artificial chromosome (Y AC) genomic libraries (Ecker, J. R., 1990, *Methods* 1, 186–194; Creusot, F., et al., 1995, *Plant J.* 8, 763–770) using the PCR (Green, E. D., et al., 1990, *Proc. Natl. Acad Sci. USA* 87, 1213–1217; Kwiatkowski, T. J., et al., 1990, *Nucleic Acidic Res.* 18, 7191–7192). Matrix based mapping results were confirmed by PCR using DNA from individual YAC clones.

mRNA Isolation. Polysomal poly(A) mRNAs from *Arabidopsis* flower, rosette leaf, inflorescence stem internode, and hydroponically-grown roots were isolated according to Cox and Goldberg (Cox, K. H., et al., 1988, in *Plant Molecular Biology. A Practical Approach*, ed. Shaw, C. H. (IRL, Oxford), pp. 1–35).

RNA Gel Blot Studies. RNA gel blot hybridizations were carried out as specified by the manufacturer (Amersham). mRNA sizes were estimated relative to known RNA standards (BRL). AP2 transcripts were detected using a labeled DNA fragment representing nucleotides 1–1371 of the AP2 cDNA plasmid clone pAP2cl (Jofuku, K. D., et al., 1994, *Plant Cell* 6, 1211–1225).

RESULTS

The AP2 Domain Defines a Large Family of Plant Proteins. Using the AP2 domain as a sequence probe 34 cDNA clones were identified that encode putative RAP2 proteins in the *Arabidopsis* EST database (Materials and Methods). Several of these partial sequences have been reported previously (Ohme-Takagi, et al., 1995, *Plant Cell* 7, 173–182; Elliot, R. C., et al., 1996, *Plant Cell* 8, 155–168; Klucher, K M., et al., 1996, *Plant Cell* 8, 137–153; Wilson, K., et al., 1996, *Plant Cell* 8, 659–671; Ecker, J. R., 1995, *Science* 268, 667–675; Weigel, D., 1995, *Plant Cell* 7, 388–389). Based on nucleotide sequence comparison, it was inferred that approximately half of the 34 RAP2 cDNA sequences were likely to represent redundant clones. Therefore, a complete DNA sequence for 17 putative RAP2 cDNA clones that appeared to represent unique genes and which contained the largest cDNA inserts was selected and generated. It was determined from the predicted amino acid sequences of these clones that the *Arabidopsis* RAP2 ESTs represent a minimum of 12 genes that are designated RAP2.1–RAP2.12. As shown in Table V, preliminary gene mapping experiments using restriction fragment length polymorphism analysis and PCR-based screening of the Arabidopsis yUP and CIC yeast artificial chromosome libraries (Materials and Methods) revealed that at least 7 members of the RAP2 gene family are distributed over 4 different chromosomes. In addition, several family members are tightly linked in the genome. For example, RAP2.10 is only 10 kb away from AP2, which is also closely linked to ANT on chromosome 4 (Elliot, R. C., et al., 1996, *Plant Cell* 8, 155–168; Klucher, K M., et al., 1996, *Plant Cell* 8, 137–153).

Sequence analysis also revealed that the proteins encoded by the RAP2 genes are all characterized by the presence of least one AP2 domain. FIG. 4 shows a sequence comparison of 21 AP2 domains from 19 different polypeptides including RAP2.1–RAP2.12, AP2, ANT, TINY, and the tobacco EREBPs. From this comparison, it was determined that there are 2 conserved sequence blocks within each AP2 domain. The first block, referred to as the YRG (SEQ ID NO:1) element, consists of 19–22 amino acids, is highly basic and contains the conserved YGR (SEQ ID NO:1) element consists of (FIGS. 4A and B). The second block, referred to as the RAYD (SEQ ID NO:8) element, is 42–43 amino acids in length and contains a highly conserved 18-amino acid core region that is predicted to form an amphipathic α-helix in the AP2 domains of AP2, ANT, TINY, and the EREBPs. In addition, there are several invariant amino acid residues within the YRG (SEQ ID NO:1) and RAYD (SEQ ID NO:8) elements that may also play a critical role in the structure or function of the proteins. For example, the *glycine* residue at position 40 within the RAYD (SEQ ID NO:8) element is invariant in all AP2 domain containing proteins (FIGS. 4A and B) and has been shown to be important for AP2 function (Jofuku, K. D., et al., 1994, *Plant Cell* 6, 1211–1225).

TABLE V

Arabidopsis RAP2 genes

| Gene | RAP2 gene containing YAC clones* | Chromosome map position† |
|---|---|---|
| AINTEGUMENTA | ND | 4-73 |
| TINY | ND | 5-32 to 5-45 |
| RAP2.1 | yUP18H2, CIC11D10 | ND‡ |
| RAP2.2 | yUP6C1 yUP12G6, yUP24B8 yUP23E11, CIC4H5, | 38§ |
| RAP2.3 | CIC12C2 | 3-21 |
| RAP2.4 | CIC7D2, CIC10C4 | ND‡ |
| RAP2.7 | yUP10E1 | ND‡ |
| RAP2.8 | CIC10G7 | 1-94 to 1-103§ |

TABLE V-continued

Arabidopsis RAP2 genes

| Gene | RAP2 gene containing YAC clones* | Chromosome map position† |
|---|---|---|
| RAP2.9 | CIC9E12 | 1-117§ |
| RAP2.10¶ | ND | 4-73 |

*YAC clones were determined to contain the specified RAP2 gene by PCR-based DNA synthesis using gene-specific primers (Green, E. D., et al., 1990, Proc. Natl. Acad Sci. USA 87, 1213–1217; Kwiatkowski, T. J., et al., 1990, Nucleic Acids Res. 18, 7191–7192).
†Chromosome map positions are given with reference to the Arabidopsis unified genetic map (AAtDB 4-7).
‡YAC-based map position is ambiguous.
§Preliminary map position is based on a single contact with the physical map.

GenBank accession numbers for complete EST sequences for RAP2 and other genes are as follows: AINTEGUMENTA (U402561U41339); TINY, (X94598), RAP2.1 (AF003094 (SEQ ID NO:100)), RAP2.2 (AF003095 (SEQ ID NO:101)), RAP2.3 (AF003096 (SEQ ID NO:102)), RAP2.4 (AF003097 (SEQ ID NO:103)), RAP2.5 (AF0030989 (SEQ ID NO:104)), RAP2.6 (AF003099(SEQ ID NO:105)), RAP2.7 (AF00310 (SEQ ID NO:106)), RAP2.8 (AF003101 (SEQ ID NO:107)), RAP2.9 (AF003102 (SEQ ID NO:108)), RAP2.10 (AF003.103(SEQ ID NO:109)), RAP2.11 (AF003104(SEQ ID NO:110)), and RAP2.12 (AF003105(SEQ ID NO:111)). All RAP2 cDNA clones were originally reported with partial sequences and given GenBank accession numbers as shown in parentheses following each gene name: RAP2.1 (Z27045), RAP2.2 (Z26440). RAP2.3 (T04320 and T13104), RAP2.4 (T13774), RAP2.5 (T45365), RAP2.6 (T45770), RAP2.7 (T20443), RAP2.8 (Z33865), RAP2.9 (Z37270), RAP2.1 (T76017), RAP2.1 (T42962), and RAP2.12 (T42544). Due to the preliminary nature of the EST sequence data, the predicted amino acid sequences for EST Z27045, T04320, T13774, and T42544 contained several errors and were incorrectly reported (Ohme-Takagi, et al., 1995, *Plant Cell* 7, 173–182; Klucher, K M., et al., 1996, *Plant Cell* 8, 137–153; Wilson, K., et al., 1996, *Plant Cell* 8, 659–671; Ecker, J. R., 1995, *Science* 268, 667–675; Weigel, D., 1995, *Plant Cell* 7, 388–389). They are correctly given in the GenBank accession numbers noted above.

RAP2 cDNA sequence comparison also shows that there are at least two branches to the RAP2 gene family tree. The AP2-like and EREBP-like branches are distinguished by the number of domains contained within each polypeptide and by sequences within the conserved YRG (SEQ ID NO:1) element. The AP2-like branch of the RAP2 gene family is comprised of three genes AP2, ANT, and RAP2.7, each of which encodes a protein containing two AP2 domains (FIG. 4A). In addition, these proteins possess a conserved WEAR/WESH (SEQ ID NO:1) acid sequence motif located in the YRG element of both AP2 domain repeats (FIG. 4A). By contrast, genes belonging to the EREBP-like branch of the RAP2 gene family encode proteins with only one AP2 domain and include RAP2.1–RAP2.6, RAP2.8–RAP2.12, and TINY(FIG. 4B). Proteins in this class possess a conserved 7-amino acid sequence motif referred to as the WAAEIRD (SEQ ID NO:8) box (FIG. 4B) in place of the WEAR/WESH (SEQ ID NO:1) motif located in the YRG (SEQ ID NO:1) element (FIG. 4A). Based on these comparisons, separate AP2 domain consensus sequences for both classes of RAP2 proteins were generated (FIGS. 4A and B). These results suggest that the AP2 domain and specific sequence elements within the AP2 domain are important for RAP2 protein functions.

The AP2-like class of RAP2 proteins is also characterized by the presence of a highly conserved 25–26 amino acid linker region that lies between the two AP2 domain repeats (Klucher, K M., et al., 1996, *Plant Cell* 8, 137–153). This region is 40% identical and 48% similar between AP2, ANT and RAP2.7 and is not found in proteins belonging to the EREBP-like branch of RAP2 proteins. Molecular analysis of the arm-3 mutant allele showed that the invariant C-terminal *glycine* residue within this linker region is essential for ANT function in vivo (Klucher, K. M., et al., 1996, *Plant Cell* 8, 137–153), suggesting that the linker region may also play an important role in AP2 and RAP2.7 function.

Sequences Within the RAYD (SEQ ID NO:8) element are Predicted to Form Amphipathic α-Helices. As noted above, the 18-amino acid core region within the RAYD element of the AP2 domain in AP2 is predicted to form an amphipathic α-helix that may be important for AP2 structure or function. Secondary structure prediction analysis was used to determine whether this structure has been conserved in RAP2 proteins. As shown in FIG. 4, the core region represents the most highly conserved sequence block in the RAYD (SEQ ID NO:8) element of AP2 and the RAP2 proteins. Secondary structure analysis predicts that all RAP2 proteins contain sequences within the RAYD (SEQ ID NO:8) element at are predicted to form amphipathic α-helices (FIGS. 4A and B). FIG. 4C shows that sequences in RAP2.7-R1 are predicted to form an amphipathic α-helix that is 100% identical to that predicted for AP2-R1 and 63% similar to that predicted for ANT-R1. Sequences within the AP2 domain of EREBP-like RAP2 proteins are predicted to form similar α-helical structures. FIG. 4D shows that the RAP2.2, RAP2.5, and RAP2.12 α-helices are 81, 100, and 81% similar to that predicted for EREBP-3, respectively. Together, these results strongly suggest that the predicted amphipathic α-helix in the RAYD (SEQ ID NO:8) element is a conserved structural motif that is important for AP2 domain function in all RAP2 proteins.

RAP2 Genes are Expressed in Floral and Vegetative Tissues. Previous studies have shown that AP2 and ANT are differentially expressed at the RNA level during plant development (Jofuku, K. D., et at., 1994, *Plant Cell* 6, 1211–1225; Elliot, R. C., et al., 1996, *Plant Cell* 8, 155–168; Klucher, K M., et al., 1996, Plant Cell 8, 137–153). AP2 is expressed at different levels in developing flowers, leaves, inflorescence stems, and roots. To determine where in plant development the EREBP-like class of RAP2 genes are expressed RAP2.1, RAP2.2, RAP2.3, and RAP2.4 gene-specific probes were reacted with a mRNA gel blot containing flower, leaf, inflorescence stem, and root polysomal poly(A) mRNA. Results from these experiments showed that each RAP2 gene produces a uniquely sized mRNA transcript and displays a distinct pattern of gene expression in flowers, leaves, inflorescence stems, and roots. For example, the RAP2.1 gene is expressed at low levels in wild-type flower, leaf, stem, and root. RAP2.2 gene expression appears to be constitutive in that RAP2.2 transcripts are detected at similar levels in wild-type flower, leaf, stem, and root. By contrast, the RAP2.3 gene is expressed at a low level in wild-type flowers, at a slightly higher level in leaves, and is relatively highly expressed in both stems and roots. Finally, the RAP2.4 gene is also expressed in wild-type flower, leaf, stem, and root and is most highly expressed in roots and leaves. These data indicate that individual members of the EREBP-like family of RAPS genes are expressed at the mRNA level in both floral and vegetative tissues and show quantitatively different patterns of gene regulation.

RAP2 Gene Expression Patterns are Affected by ap2. RAP2 gene expression was analyzed in ap2–10 mutant plants by RNA gel blot analysis to determine whether AP2 is required for RAP2 gene expression. The expression of three RAP2 genes are differentially affected by the loss of AP2 function. For example, RAP2.2 gene expression is not dramatically altered in mutant flowers, leaves, and roots compared to wild-type Landsberg erecta but is down-regulated in mutant stem. RAP2.3 gene expression appears unchanged in mutant roots but is tip-regulated in mutant flowers and leaves and down-regulated in mutant stems. By contrast, RAP2.4 gene expression appears relatively unchanged in mutant stems and roots but is slightly up-regulated in mutant flowers and leaves. To control for possible secondary effects of ecotype on RAP2 gene expression, RAP2 gene expression levels in wild-type C24 and ap2–10 mutant stems were compared. These results show that the differences in RAP2.2 RAP2.3, and RAP2.4 gene expression in C24 and ap2–10 stem are similar to those observed between wild-type Landsberg erecta and ap2–10 mutant stein. Together these results suggest that AP2 directly or indirectly regulates the expression of at least three RAP2 genes. More importantly, these results suggest that AP2 is controlling gene expression during both reproductive and vegetative development.

DISCUSSION

RAP2 Genes Encode a New Family of Putative DNA Binding Proteins.

One important conclusion from the characterization of these clones is that the AP2 domain has been evolutionarily conserved in at least Arabidopsis and tobacco. In addition, there are two subfamilies of AP2 domain containing proteins in *Arabidopsis* that are designated as the AP2-like and the EREBP-like class of RAP2 proteins. In vitro studies have shown that both the EREBP and the AP2 proteins bind to DNA in a sequence specific manner and that the AP2 domain is sufficient to confer EREBP DNA binding activity (Ohme-Takagi, et al., 1995, *Plant Cell* 7, 173–182). From these results and the high degree of sequence similarity between the AP2 domain motifs in AP2, the EREBPs and the RAP2 proteins, it is concluded that RAP2 proteins function as plant sequence specific DNA binding proteins. Although the exact amino acid residues within the AP2 domain required for DNA binding have not yet been identified, sequence comparisons have revealed two highly conserved motifs referred to it as the YRG (SEQ ID NO:1) and RAYD (SEQ ID NO:8) elements within the AP2 domain The RAYD (SEQ ID NO:8) element is found in all known AP2 domains and contains a conserved core region that is predicted to form an amphipathic α-helix (FIG. 4). One hypothesis for the function of this α-helical structure is that it is involved in DNA binding, perhaps through the interaction of its hydrophobic face with the major groove of DNA (Zubay, G., et al., 1959, *J. Mol. Biol.* 7, 1–20). Alternatively, this structure may mediate protein-protein interactions important for RAP2 functions. These interaction may involve the ability to form homo- or heterodimers similar to that observed for the MADS (SEQ ID NO:99) box family of plant regulatory proteins (Huang, H., et al., 1996, *Plaint Cell* 8, 81–94; Riechmann, J. L, et al., 1996, *Proc. Natl. Acad. Sci. USA* 93, 4793–4798) and for the mammalian ATF/CREB family of transcription factors (Hai, T., et al., 1991, *Proc. Natl. Acad. Sci. USA* 88, 37203724 O'Shea, E. K, et al., 1992, *Cell* 68, 699–708.).

The conserved YRG (SEQ ID NO:1) element may also function in DNA binding due to the highly basic nature of this region in all RAP2 proteins (FIG. 4). However, the YRG element also contains sequences that are specific for each class of RAp2 protein and may be functionally important for DNA binding. Specifically, the WAAJERD (SEQ ID NO:98) motif is highly conserved in tobacco EREBPs and in EREBP-like RAP2 proteins. By contrast, the WEAR/WESH (SEQ ID NO:2) motif replaces the WAAIERD (SEQ ID NO:98) box in AP-like RAP2 proteins (FIG. 4). In vitro studies suggest that the EREBPs and AP2 recognize distinct DNA sequence elements (Ohme-Takagi, et al., 1995, *Plant Cell* 7, 173–182). It is possible that the WAAIERD (SEQ ID NO:98) and WEAR/WESH motifs may be responsible for DNA binding sequence specificity. The presence of two AP2 domains in AP2 may also contribute to differences in sequence specificity. Although the molecular significance of having one or two AP2 domain motifs is not yet known, genetic and Molecular studies have shown that mutations in either AP2 domain affect AP2 function, implying that both are required for wild-type AP2 activity (Jofuku, K. D., et al., 1994, *Plant Cell* 6, 1211–1225).

In addition to Arabidopsis and tobacco, cDNAs that encode diverse AP2 domain-containing proteins have been found in maize, rice, castor bean, and several members of the Brassicaceae including canola (Ohme-Takagi, et al., 1995, *Plant Cell* 7, 173–182; Elliot, R. C., et al., 1996, *Plant Cell* 8, 155–168; Klucher, K M., et al., 1996, *Plant Cell* 8, 137–153; Wilson, K., et al., 1996, *Plant Cell* 8, 659–671 and Weigel, D., 1995, *Plant Cell* 7, 388–389). This strongly suggests that the AP2 domain is an important and evolutionarily conserved element necessary for the structure or function of these proteins.

RAP2 Gene Expression in Floral and Vegetative Tissues. The AP2, RAP2.1, RAP2.2, RAP2.3, and RAP2.4 genes show overlapping patterns of gene expression at the mRNA level in flowers, leaves, inflorescence stems, and roots. However, each gene appears to be differentially regulated in terms of its mRNA prevalence. The overlap in RAP2 gene activity could affect the genetic analysis of AP2 and RAP2 gene functions if these genes are also functionally redundant. For example, in flower development AP2 and ANT show partially overlapping patterns of gene expression at the organ and tissue levels (Jofuku, K. D., et al., 1994, *Plant Cell* 6, 1211–1225; Elliot, R. C., et al., 1996, *Plant Cell* 8, 155–168; Klucher, K M., et al., 1996, *Plant Cell* 8, 137–153; W. Szeto). From single and double mutant analysis it has also been suggested that AP2 may be partially redundant in function with ANT (Elliot, R. C., et al., 1996, *Plant Cell* 8, 155–168). The phenomenon of genetic redundancy and its ability to mask the effects of gene mutation is more clearly demonstrated by the MADS domain containing floral regulatory genes APETALA1 (AP1) and CAULIFLOWER (CAL). Genetic studies have demonstrated that mutations in call show no visible floral phenotype except when in double mutant combination with ap1 (Bowman, J. L, et al., 1993, *Development Cambridge, U.K.,* 119, 721–743), indicating that AP1 is completely redundant in function for CAL. The hypothesis that the RAP2 genes may have genetically redundant functions is supported by the fact that the dominant gain-of-function mutation tiny is the only *Arabidopsis* RAP2 EREBP-like gene mutant isolated to date (Wilson, K., et al., 1996, *Plant Cell* 8, 659–671).

AP2 Activity Is Detectable in Vegetative Development. The present analysis of RAP2 gene expression in wild-type and ap2–10 plants suggests that AP2 contributes to the regulation of RAP2 gene activity throughout *Arabidopsis* development. RAP2 gene expression is both positively and negatively affected by the absence of AP2 activity during development. The observed differences in RAP2.2, RAP2.3, and RAP2.4 gene expression levels in wild-type and ap2–10 flowers and vegetative tissues are not apparently due to differences in ecotype because similar changes in gene expression levels were observed for all three RAP2 genes in stems when ecotype was controlled. The regulation of RAP2 gene expression by AP2 in stems clearly indicates that unlike other floral homeotic genes AP2 functions in both reproductive and vegetative development.

This example shows that transgenic plants of the invention bear seed with altered fatty acid content and composition.

Antisense transgenic plants were prepared using A P2, RAP2.8, and RAP2.1 (two independent plants) using methods described above. The fatty acid content and composition were determined using gas chromatography as described Broun and Somerville *Plant Physiol.* 113:933–942 (1997). The results are shown in Table VI (for AP2) and Table VII (for the RAP2 genes). As can be seen there, the transgenic plants of the invention have increased fatty acid content as compared to wild-type plants. In addition, the profile of fatty acids is altered in the plants.

TABLE VI

Analysis of Arabidopsis seed fatty acid content and composition.

| Plants | Seed Mass (μg/seed) | Total Fatty Acid Content (μg/seed) | Fatty acid methyesters (%) (area % by GLC) | | | | | | | |
|---|---|---|---|---|---|---|---|---|---|---|
| | | | 16:0 | 18:0 | 18:1 | 18:2 | 18:3 | 20:1 | 22:1 | 24:0 |
| Mutant | | | | | | | | | | |
| ap2-10 αAP2 transgenic plants | 27 | 3.94 | 9.4 | 4.4 | 2.5 | 70.8 | 0.8 | 6.6 | 0.1 | 1.9 |
| C24 15-522 (F1-1) | 34 | 11.0 | 4.5 | 3.3 | 3.1 | 49.0 | 3.2 | 26.3 | 0.6 | 4.9 |
| C34 15-542 (F1-2) | 24 | 2.5 | 6.3 | 3.4 | 3.1 | 52.1 | 4.0 | 28.1 | 0.4 | 0.4 |
| Wild-type | | | | | | | | | | |
| C24 | 20 | 2.67 | 9.4 | 4.9 | 8.8 | 62.7 | 0.7 | 8.1 | 0.3 | 1.9 |

TABLE VII

Analysis of Arabidopsis RAP2 antisense transgenic seed fatty acid content and composition.

| Plants | Seed Mass (μg/seed) | Total Fatty Acid Content (μg/seed) | Fatty acid methyesters (%) (area % by GLC) | | | | | | | |
|---|---|---|---|---|---|---|---|---|---|---|
| | | | 16:0 | 18:0 | 18:1 | 18:2 | 18:3 | 20:1 | 22:1 | 24:0 |
| RAP2 antisense transgenic plants | | | | | | | | | | |
| RAP34-2.8C LE | 24 | 9.7 | 5.1 | 3.0 | 3.6 | 53.6 | 3.2 | 29.3 | 0.3 | 0.2 |
| RAP34-2.1A' COL | 34 | 11.0 | 9.5 | 1.9 | 3.0 | 53.6 | 4.2 | 20.3 | 5.5 | 0.5 |
| RAP34-2.1D' COL | 26 | 8.1 | 4.6 | 2.6 | 2.6 | 50.3 | 3.2 | 33.2 | 0.3 | 1.0 |
| Wild-type | | | | | | | | | | |
| COL[a] | 24 | ND | 6.0 | 4.0 | 14.0 | 27.0 | 18.0 | 22.0 | 2.0 | ND |

ND not determined
[a]Patak et al. (1994) Oil content and fatty acid composition of seeds of various ecotypes of *Arabidopsis thaliana*: a search for useful genetic variants. Curr. Sci. 67, 470–472.

EXAMPLE 6

This example describes construction of promoter construct which are used to prepare expression cassettes useful in making transgenic plants of the invention. In particular, this example shows use of two preferred promoters, the promoter from the AP2 gene and the promoter from the Bell gene.

Figure 5:
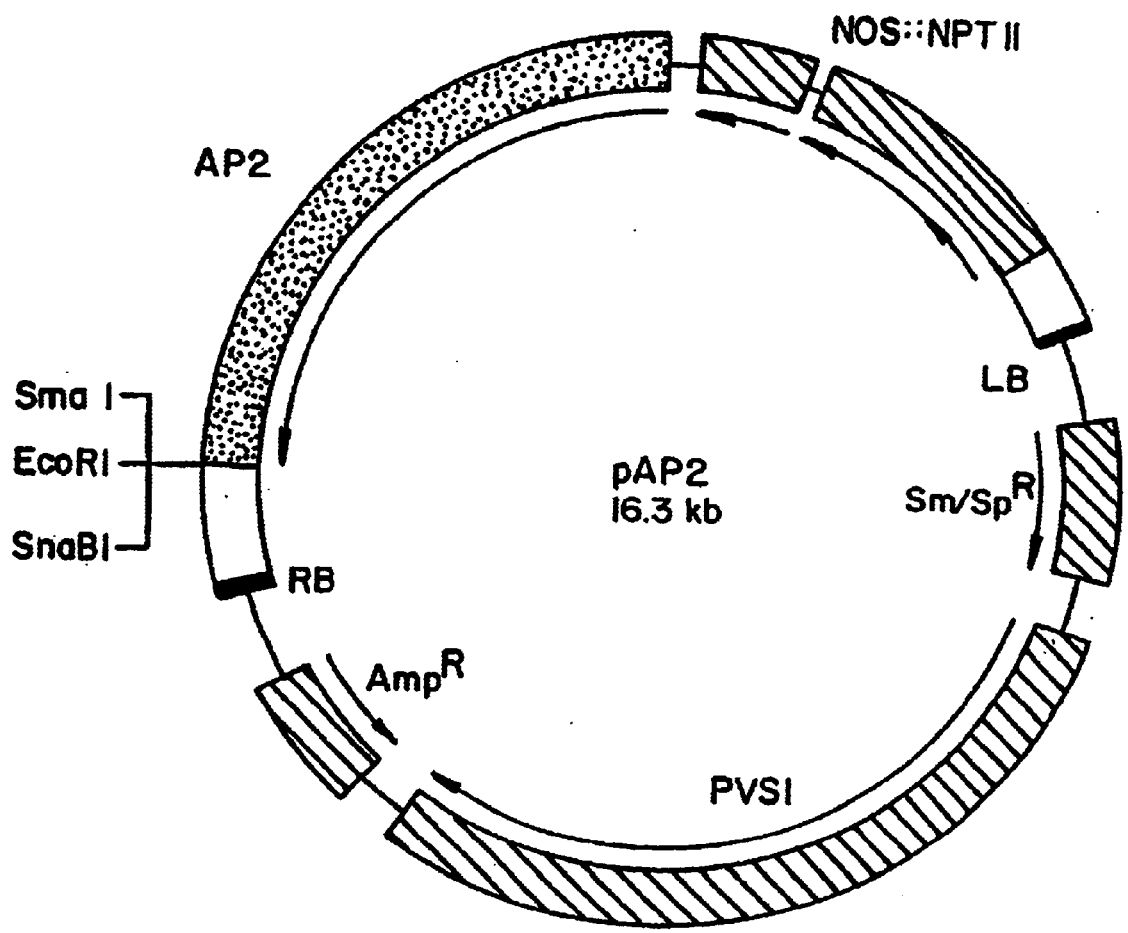
FIG. 5 is a schematic diagram of pAP2, which can be used to construct expression vectors of the invention.

FIG. 5 shows a AP2 promoter construct. pAP2 represents the 16.3 kb AP2 promoter vector cassette that is used to generate chimeric genes for use in plant transformations described here. pAP2 is comprised of the 4.0 kb promoter region of the *Arabidopsis* AP2 gene. The Ti plasmid vector used is pDE1000 vector (Plant Genetic Systems, Ghent, Belgium). The pDE1000 vector DNA was linearized with BamH1 and the AP2 promoter region inserted as a 4.0 kb BamH1 DNA fragment from plasmid subclone pLE7.2. At the 3' end of the inserted AP2 promoter region, designated AP2, lie three restriction sites (EcoR1, Sma1 and SnaB1) into which different gene coding regions can be inserted to generate chimeric AP2 promoter/gene cassettes. NOS::NPTII represents the plant selectable marker gene NPTII under the direction of the nopaline synthase promoter which confers resistance to the antibiotic kanamycin to transformed plants cells carrying an integrated AP2 promoter cassette. LB and RB represent the T-DNA left and right border sequences, respectively, that are required for transfer of T-DNA containing the AP2 promoter cassette into the plant genome. PVS1 designates the bacterial DNA sequences that function as a bacterial origin of replication in both *E. coli* and *Agrobacterium tumefaciens*, thus allowing pAP2 plasmid replication and retention in both bacteria. $Amp^R$ and $Sm/Sp^R$ designate bacterial selectable marker genes that confer resistance to the antibiotics ampicillin and streptomycin/spectinomycin, respectively, and allows for selection of Agrobacterium strains that carry the pAP2 recombinant plasmid.

Figure 6:
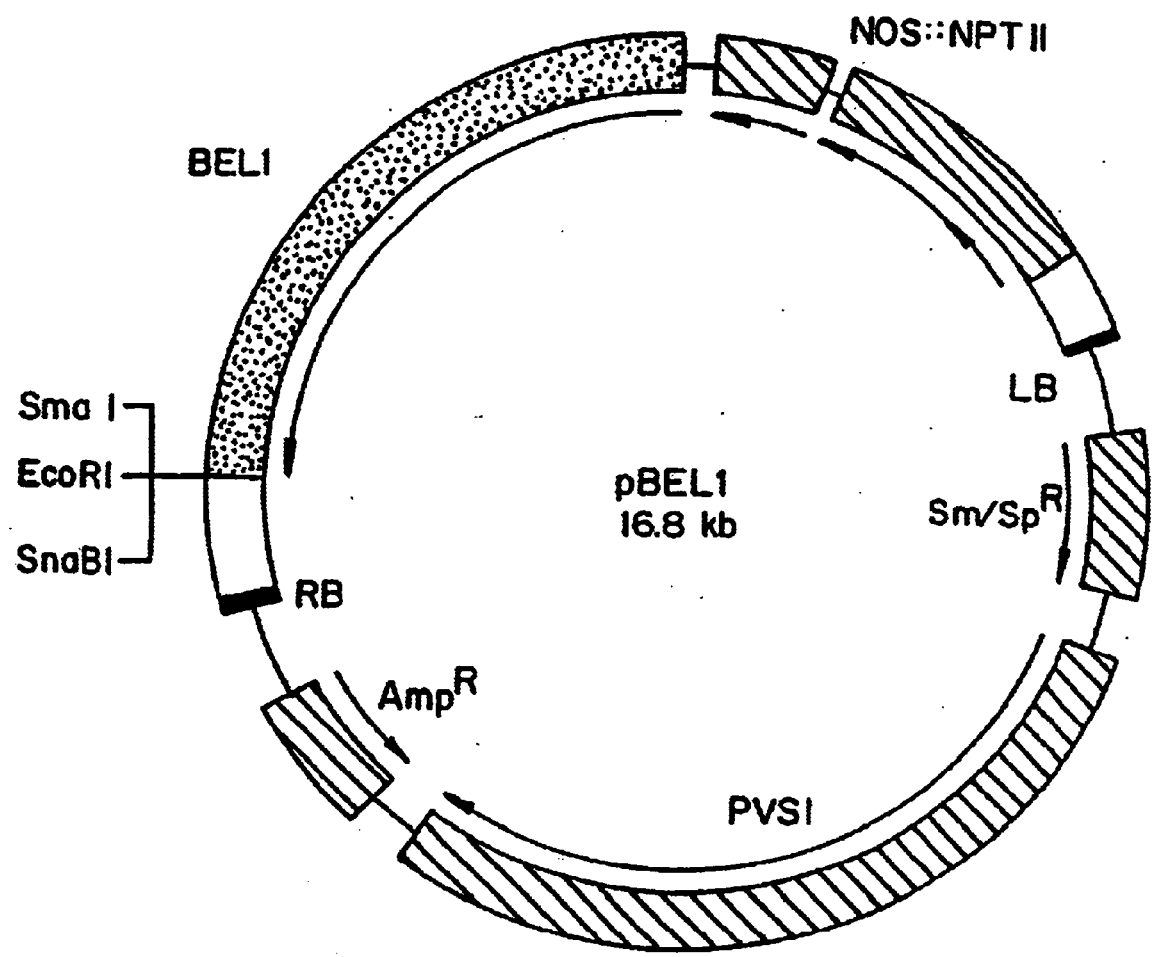
FIG. 6 is a schematic diagram of pBEL1, which can be used to construct expression vectors of the invention.

FIG. 6 shows a BEL1 promoter constrict. pBEL1 represents the 16.8 kb BEL1 promoter vector cassette that is used to generate chimeric genes for use in plant transformations described here. pBEL1 is comprised of the 4.5 kb promoter region of the *Arabidopsis* BEL1 gene. The Ti plasmid vector used is pDE1000 vector (Plant Genetic Systems, Ghent, Belgium). The pDE1000 vector DNA was linearized will BamH1 and the BEL1 promoter region inserted as a 4.5 kb BamH 1-Bg12 DNA fragment from plasmid subclone pλ1C9R (L. Reiser, unpublished). At the 3' end of the inserted BEL1 promoter region, designated BEL1, lie three restriction sites (EcoR1, Sma1 and SnaB1) into which different gene coding regions can be inserted to generate chimeric BEL promoter/gene cassettes. NOS::NPTII represents the plant selectable marker gene NPTII under the direction of the nopaline synthase promoter which confers resistance to the antibiotic kanamycin to transformed plants cells carrying an integrated BEL promoter cassette. LB and RB represent the T-DNA left and right border sequences, respectively, that are required for transfer of T-DNA containing the BEL promoter cassette into the plant genome. PVS1 designates the bacterial DNA sequences that function as a bacterial origin of replication in both *E. coli* and *Agrobacterium tumefaciens*, thus allowing pBEL plasmid replication and retention in both bacteria. $Amp^R$ and $Sm/SP^R$ designate bacterial selectable marker genes that confer resistance to the antibiotics ampicillin and streptomycin/spectinomycin, respectively, and allows for selection of Agrobacterium strains that carry the pBEL recombinant plasmid.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of modulating seed mass or oil content in a plant, the method comprising:
providing a first plant comprising a recombinant expression cassette containing an ADC nucleic acid linked to a plant promoter, which ADC nucleic acid comprises a nucleic acid sequence at least about 80% identical to a nucleic acid sequence selected from a group consisting of SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID N O109, SEQ ID NO 110, and SEQ ID NO:111, and which ADC nucleic acid encodes a polypeptide that module seed mass or oil content;
selfing the first plant or crossing the first plant with a second plant, thereby producing a plurality of seeds; and
selecting seed with altered mass or oil content.

2. The method of claim 1, wherein expression of the ADC nucleic acid inhibits expression of an endogenous ADC gene and the step of selecting includes the step of selecting seed with increased mass.

3. The method of claim 2, wherein the seed have increased protein content, carbohydrate content, or oil content.

4. The method of claim 2, wherein the ADC nucleic acid is linked to the plant promoter in the antisense orientation.

5. The method of claim 2, wherein the fiat and second plants are the same species.

6. The method of claim 2, wherein the first and second plants are members of the family Brassicaccae.

7. The method of claim 2, wherein the first and second plants are members of the family Solanacoae.

8. The method of claim 2, wherein the plant promoter is a constitutive promoter.

9. The method of claim 8, wherein the promoter is a CaMV 35S promoter.

10. The method of claim 2, wherein the promoter is a tissue-specific promoter.

11. The method of claim 10, wherein the promoter is ovule-specific.

12. A seed produced by the method of claim 2.

13. The method of claim 1, wherein expression of the ADC nucleic acid enhances expression of an endogenous ADC gene and the step of selecting includes the step of selecting seed with decreased mass.

14. The method of claim 13, wherein the first and second plants are the same species.

15. The method of claim 13, wherein the first and second plants are members of the family Brassicaceae.

16. The method of claim 13, wherein the first and second plants are members of the family Solanaceae.

17. The method of claim 13, wherein the plant promoter is a constitutive promoter.

18. The method of claim 17, wherein the promoter is a CaMV 35S promoter.

19. The method of claim 13, wherein the promoter is a tissue specific promoter.

20. The method of claim 19, wherein the promoter is ovule-specific.

21. A seed produced by the method of claim 13.

22. A seed comprising a recombinant expression cassette containing an ADC nucleic acid, which ADC nucleic acid comprises a nucleic acid sequence at least about 80% identical to a nucleic acid sequence selected from a group consisting of SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO109, SEQ ID NO 110, and SEQ ID NO:111, and which ADC nucleic acid encodes a polypeptide that modulates seed mass or oil content, with the proviso that the seed is not from *Arabidopsis*.

23. The seed of claim 22, which is derived from a plant that is a member of the family *Brassicaceae*.

24. The seed of claim 22, wherein the ADC nucleic acid is linked to a plant promoter in an antisense orientation and the seed mass is at least about 10% greater than the average mass of seeds from the same plant variety which lack the recombinant expression cassette.

25. The seed of claim 24, wherein the mass is at least about 20% greater than the average mass of seeds from the same plant variety which lack the recombinant expression cassette.

26. The seed of claim 24, wherein the mass is at least about 50% greater than the average mass of seeds from the same plant variety which lack the recombinant expression cassette.

27. The seed of claim 24, wherein the oil content is proportionally increased.

28. The seed of claim 24, wherein the protein content is proportionally increased.

29. The seed of claim 22, wherein the ADC nucleic acid is linked to a plant promoter in the sense orientation and the seed mass is at least about 10% less than the average mass of seeds of the same plant variety which lack the recombinant expression cassette.

30. The seed of claim 29, which has a mass at least about 20% less than the average mass of seeds of the same plant variety which lack the recombinant expression cassette.

31. The seed of claim 29, which has a mass at least about 50% less than the average mass of seeds of the same plant variety which lack the recombinant expression cassette.

32. A transgenic plant comprising an expression cassette containing a plant promoter operably linked to a heterologous ADC nucleic acid, when the ADC nucleic acid comprises a nucleic acid sequence at least about 80% identical to a nucleic acid sequence selected from a group consisting of SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO109, SEQ ID NO 110, and SEQ ID NO:111, and which ADC nucleic acid encodes a polypeptide that modulates seed mass or oil content, with the proviso that the transgenic plant is not *Arabidopsis*.

33. The transgenic plant of claim 32, wherein the heterologous ADC polynucleotide encodes a ADC polypeptide.

34. An isolated nucleic acid molecule comprising an expression cassette containing a plant promoter operably linked to a heterologous ADC nucleic acid comprises a nucleic acid sequence at least about 80% identical to a nucleic acid sequence selected from a group containing of SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO109, SEQ ID NO 110, and SEQ ID NO:111, and which ADC nucleic acid encodes a polypeptide that modulates seed mass or oil content.

35. A method of modulating seed oil content in a plant, the method comprising:
providing a first plant comprising a recombinant expression cassette containing an ADC nuclei acid linked to a plant promoter, which ADC nucleic acid comprises a nucleic acid sequence at least about 80% identical to a nucleic acid sequence selected from a group consisting of SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO109, SEQ ID NO 110, and SEQ ID NO:111, and which ADC nucleic acid encodes polypeptide that modulates seed mass or oil content;
selfing the first plant or comprising the first plant with a second plant, thereby producing a plurality of seeds; and
selecting seed with altered oil content.

36. The method of claim 1, wherein the ADC nucleic acid is SEQ ID NO:100.

37. The method of claim 1, wherein the ADC nucleic acid is SEQ ID NO:101.

38. The method of claim 1, wherein the ADC nucleic acid is SEQ ID NO:102.

39. The method of claim 1, wherein the ADC nucleic acid is SEQ ID NO:103.

40. The method of claim 1, wherein the ADC nucleic acid is SEQ ID NO:104.

41. The method of claim 1, wherein the ADC nucleic acid SEQ ID NO:105.

42. The method of claim 1, wherein the ADC nucleic acid is SEQ ID NO:106.

43. The method of claim 1, wherein the ADC nucleic acid is SEQ ED NO:107.

44. The method of claim 1, wherein the ADC nucleic acid is SEQ ID NO:108.

45. The method of claim 1, wherein the ADC nucleic acid is SEQ ID NO:109.

46. The method of claim 1, wherein the ADC nucleic acid is SEQ ID NO:110.

47. The method of claim 1, wherein the ADC nucleic acid is SEQ ID NO:111.

48. The method of claim 13, wherein the ADC nucleic acid is SEQ ID NO:100.

49. The method of claim 13, wherein the ADC nucleic acid is SEQ ID NO:101.

50. The method of claim 13, wherein the ADC nucleic acid is SEQ ID NO:102.

51. The method of claim 13, wherein the ADC nucleic acid is SEQ ID NO:103.

52. The method of claim 13, wherein the ADC nucleic acid is SEQ ID NO:104.

53. The method of claim 13, wherein the ADC nucleic acid is SEQ ID NO:105.

54. The method of claim 13, wherein the ADC nucleic acid is SEQ ID NO:106.

55. The method of claim 13, wherein the ADC nucleic acid is SEQ ID NO:107.

56. The method of claim 13, wherein the ADC nucleic acid is SEQ ID NO:108.

57. The method of claim 13, wherein the ADC nucleic acid is SEQ ID NO:109.

58. The method of claim 13, wherein the ADC nucleic acid is SEQ ID NO:110.

59. The method of claim 13, wherein the ADC nucleic acid is SEQ ID NO:111.

60. The seed of claim 22, wherein the ADC nucleic acid is SEQ ID NO:100.

61. The seed of claim 22, wherein the ADC nucleic acid is SEQ ID NO:101.

62. The seed of claim 22, wherein the ADC nucleic acid is SEQ ID NO:102.

63. The seed of claim 22, wherein the ADC nucleic acid is SEQ ID NO:103.
64. The seed of claim 22, wherein the ADC nucleic acid is SEQ ID NO:104.
65. The seed of claim 22, wherein the ADC nucleic acid is SEQ ID NO:105.
66. The seed of claim 22, wherein the ADC nucleic acid is SEQ ID NO:106.
67. The seed of claim 22, wherein the ADC nucleic acid is SEQ ID NO:107.
68. The seed of claim 22, wherein the ADC nucleic acid is SEQ ID NO:108.
69. The seed of claim 22, wherein the ADC nucleic acid is SEQ ID NO:109.
70. The seed of claim 22, wherein the ADC nucleic acid is SEQ ID NO:110.
71. The seed of claim 22, wherein the ADC nucleic acid is SEQ ID NO:111.
72. The transgenic plant of claim 32, wherein the ADC nucleic acid is SEQ ID NO:100.
73. The transgenic plant of claim 32, wherein the ADC nucleic acid is SEQ ID NO:101.
74. The transgenic plant of claim 32, wherein the ADC nucleic acid is SEQ ID NO:102.
75. The transgenic plant of claim 32, wherein the ADC nucleic acid is SEQ ID NO:103.
76. The transgenic plant of claim 32, wherein the ADC nucleic acid is SEQ ID NO:104.
77. The transgenic plant of claim 32, wherein the ADC nucleic acid is SEQ ID NO:105.
78. The transgenic plant of claim 32, wherein the ADC nucleic acid is SEQ ID NO:106.
79. The transgenic plant of claim 32, wherein the ADC nucleic acid is SEQ ID NO:107.
80. The transgenic plant of claim 32, wherein the ADC nucleic acid is SEQ ID NO:108.
81. The transgenic plant of claim 32, wherein the ADC nucleic acid is SEQ ID NO:109.
82. The transgenic plant of claim 32, wherein the ADC nucleic acid is SEQ ID NO:110.
83. The transgenic plant of claim 32, wherein the ADC nucleic acid is SEQ ID NO:111.
84. The isolated nucleic acid of claim 34, wherein the ADC nucleic acid is SEQ ID NO:100.
85. The isolated nucleic acid of claim 34, wherein the ADC nucleic acid is SEQ ID NO:101.
86. The isolated nucleic acid of claim 34, wherein the ADC nucleic acid is SEQ ID NO:102.
87. The isolated nucleic acid of claim 34, wherein the ADC nucleic acid is SEQ ID NO:103.
88. The isolated nucleic acid of claim 34, wherein the ADC nucleic acid is SEQ ID NO:104.
89. The isolated nucleic acid of claim 34, wherein the ADC nucleic acid is SEQ ID NO:105.
90. The isolated nucleic acid of claim 34, wherein the ADC nucleic acid is SEQ ID NO:106.
91. The isolated nucleic acid of claim 34, wherein the ADC nucleic acid is SEQ ID NO:107.
92. The isolated nucleic acid of claim 34, wherein the ADC nucleic acid is SEQ ID NO:108.
93. The isolated nucleic acid of claim 34, wherein the ADC nucleic acid is SEQ ID NO:109.
94. The isolated nucleic acid of claim 34, wherein the ADC nucleic acid is SEQ ID NO:10.
95. The isolated nucleic acid of claim 34, wherein the ADC nucleic acid is SEQ ID NO:111.

* * * * *

UNITED STATES PATENT AND TRADEMARK OFFICE
CERTIFICATE OF CORRECTION

PATENT NO. : 6,846,669 B1
DATED : January 25, 2005
INVENTOR(S) : K. Diane Jofuku et al.

It is certified that error appears in the above-identified patent and that said Letters Patent is hereby corrected as shown below:

Column 8,
Line 8, kindly insert -- This invention was made with Government support under Grant No. GM46309 and GM08132, awarded by the National Institutes of Health. The Government has certain rights in this invention. --

Signed and Sealed this

Thirty-first Day of May, 2005

JON W. DUDAS
*Director of the United States Patent and Trademark Office*

SEQUENCE LISTING (1) GENERAL INFORMATION:

(iii) NUMBER OF SEQUENCES: 111

(2) INFORMATION FOR SEQ ID NO:1:

(i) SEQUENCE CHARACTERISTICS:
      (A) LENGTH: 3 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Tyr Arg Gly
1

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: 3
      (D) OTHER INFORMATION: /product= "OTHER"
         /note= "Xaa = Ala or Ser"

(ix) FEATURE:
      (A) NAME/KEY: Modified-site
      (B) LOCATION: 4
      (D) OTHER INFORMATION: /product= "OTHER"
         /note= "Xaa = Arg or His"

(xi) SEQUENCE DESCRIPTION: SEQ ID NO:2:

Trp Glu Xaa Xaa
1

(2) INFORMATION FOR SEQ ID NO:3:

(i) SEQUENCE CHARACTERISTICS:
      (A) LENGTH: 1680 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: -
      (B) LOCATION: 1..1680
      (D) OTHER INFORMATION: /note= "Arabidopsis APETALA2 (AP2)"

(xi) SEQUENCE DESCRIPTION: SEQ ID NO:3:

```
CTCTCTCTCT CTCTTTAGCT CTTTTTTTTT TTTTGTTTTC ATTAAAGTTT TTATTTTATT      60

TTCTACCAAC CAAAAGCTTT TCTCTTTGGT TTCTCTTATT TAGCTTCTAA CCTTGAGGAG     120

AATATACCAG AGGATTGAAG TTTGAACCTT CAAAGATCAA AATCAAGAAA CCAAAAAAAA     180

ACAAAAAAAA TGTGGGATCT AAACGACGCA CCACACCAAA CACAAAGAGA AGAAGAATCT     240

GAAGAGTTTT GTTATTCTTC ACCAAGTAAA CGGGTTGGAT CTTTCTCTAA TTCAAGCTCT     300
```

```
TCAGCTGTTG TTATCGAAGA TGGATCCGAT GACGATGAAC TTAACCGGGT CAGACCCAAT    360

AACCCACTTG TCACCCATCA GTTCTTCCCT GAGATGGATT CTAACGGCGG TGGTGTTGCT    420

TCTGGCTTTC CTCGGGCTCA CTGGTTTGGT GTTAAGTTTT GTCAGTCGGA TCTAGCCACC    480

GGATCGTCCG CGGGTAAAGC TACCAACGTT GCCGCTGCCG TAGTGGAGCC GGCACAGCCG    540

TTGAAAAAGA GTCGGCGTGG ACCAAGATCA AGAAGTTCTC AGTATAGAGG TGTTACGTTT    600

TACCGGCGTA CCGGAAGATG GGAATCTCAT ATTTGGGACT GTGGGAAACA AGTTTACTTA    660

GGTGGATTTG ACACTGCTCA TGCAGCAGCT CGAGCATATG ATAGAGCTGC TATTAAATTC    720

CGTGGAGTAG AAGCGGATAT CAATTTCAAC ATCGACGATT ATGATGATGA CTTGAAACAG    780

ATGACTAATT TAACCAAGGA AGAGTTCGTA CACGTACTTC GCCGACAAAG CACAGGCTTC    840

CCTCGAGGAA GTTCGAAGTA TAGAGGTGTC ACTTTGCATA AGTGTGGTCG TTGGGAAGCT    900

CGTATGGGTC AATTCTTAGG CAAAAAGTAT GTTTATTTGG GTTTGTTCGA CACCGAGGTC    960

GAAGCTGCTA GAGCTTACGA TAAAGCTGCA ATCAAATGTA ACGGCAAAGA CGCCGTGACC   1020

AACTTTGATC CGAGTATTTA CGATGAGGAA CTCAATGCCG AGTCATCAGG GAATCCTACT   1080

ACTCCACAAG ATCACAACCT CGATCTGAGC TTGGGAAATT CGGCTAATTC GAAGCATAAA   1140

AGTCAAGATA TGCGGCTCAG GATGAACCAA CAACAACAAG ATTCTCTCCA CTCTAATGAA   1200

GTTCTTGGAT TAGGTCAAAC CGGAATGCTT AACCATACTC CCAATTCAAA CCACCAATTT   1260

CCGGGCAGCA GCAACATTGG TAGCGGAGGC GGATTCTCAC TGTTTCCGGC GGCTGAGAAC   1320

CACCGGTTTG ATGGTCGGGC CTCGACGAAC CAAGTGTTGA CAAATGCTGC AGCATCATCA   1380

GGATTCTCTC CTCATCATCA CAATCAGATT TTTAATTCTA CTTCTACTCC TCATCAAAAT   1440

TGGCTGCAGA CAAATGGCTT CCAACCTCCT CTCATGAGAC CTTCTTGAAT CTTTTATATT   1500

TTTAAGGTTT ATTATTATAT AAGAAAAACA AAAATGAACC TTTGAAATCC CCACATGTTC   1560

TTGGTCATTT CATTAATCAT CGGCTTATAT TTTGCTTATT TTCCCCTAAA TCCTCTTGTT   1620

AACTTAGGCG AACAAAAAAA ATTAATGGAA ATCTTTTTCC CTCCATCGGT TACAAAAATA   1680
```

(2) INFORMATION FOR SEQ ID NO:4:

(i) SEQUENCE CHARACTERISTICS:
        (A) LENGTH: 67 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..67
        (D) OTHER INFORMATION: /note= "AP2-R1 direct repeat at
            positions 129 to 195"

(ix) FEATURE:
        (A) NAME/KEY: Region
        (B) LOCATION: 32..49
        (D) OTHER INFORMATION: /note= "putative AP2-R1 amphipathic
            alpha-helix (SEQ ID NO:6)"

(xi) SEQUENCE DESCRIPTION: SEQ ID NO:4:

```
Ser Ser Gln Tyr Arg Gly Val Thr Phe Tyr Arg Arg Thr Gly Arg Trp
1               5                  10                  15

Glu Ser His Ile Trp Asp Cys Gly Lys Gln Val Tyr Leu Gly Gly Phe
            20                  25                  30

Thr Asp Ala His Ala Ala Ala Arg Ala Tyr Asp Arg Ala Ala Ile Lys
        35                  40                  45
```

```
Phe Arg Gly Val Glu Ala Asp Ile Asn Phe Asn Ile Asp Asp Tyr Asp
 50                  55                  60

Asp Asp Leu
 65
```

(2) INFORMATION FOR SEQ ID NO:5:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "AP2-R2 direct repeat at
            positions 221 to 288"

(ix) FEATURE:
        (A) NAME/KEY: Region
        (B) LOCATION: 33..50
        (D) OTHER INFORMATION: /note= "putative AP2-R2 amphipathic
            alpha-helix (SEQ ID NO:7)"

(xi) SEQUENCE DESCRIPTION: SEQ ID NO:5:

```
Ser Ser Lys Tyr Arg Gly Val Thr Leu His Lys Cys Gly Arg Trp Glu
 1               5                  10                  15

Ala Arg Met Gly Gln Phe Leu Gly Lys Lys Tyr Val Tyr Leu Gly Leu
             20                  25                  30

Phe Asp Thr Glu Val Glu Ala Ala Arg Ala Tyr Asp Lys Ala Ala Ile
             35                  40                  45

Lys Cys Asn Gly Lys Asp Ala Val Thr Asn Phe Asp Pro Ser Ile Tyr
 50                  55                  60

Asp Glu Glu Leu
 65
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..18
        (D) OTHER INFORMATION: /note= "putative AP2-R1 amphipathic
            alpha-helix"

(xi) SEQUENCE DESCRIPTION: SEQ ID NO:6:

```
Phe Asp Thr Ala His Ala Ala Ala Arg Ala Tyr Asp Arg Ala Ala Ile
 1               5                  10                  15

Lys Phe
```

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS:
        (D) TOPOLOGY: linear

```
    (ii) MOLECULE TYPE: peptide (ix) FEATURE:
         (A) NAME/KEY: Peptide
         (B) LOCATION: 1..18
         (D) OTHER INFORMATION: /note= "putative AP2-R2 amphipathic
             alpha-helix"

(xi) SEQUENCE DESCRIPTION: SEQ ID NO:7:

Phe Asp Thr Glu Val Glu Ala Ala Arg Ala Tyr Asp Lys Ala Ala Ile
1               5                  10                  15

Lys Cys (2) INFORMATION FOR SEQ ID NO:8:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:8:

Arg Ala Tyr Asp
1

(2) INFORMATION FOR SEQ ID NO:9:

(i) SEQUENCE CHARACTERISTICS:
         (A) LENGTH: 77 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..77
         (D) OTHER INFORMATION: /note= "ANT-R1 direct repeat"

(ix) FEATURE:
         (A) NAME/KEY: Region
         (B) LOCATION: 44..59
         (D) OTHER INFORMATION: /note= "putative ANT-R1 amphipathic
             alpha-helix (SEQ ID NO:37)"

(xi) SEQUENCE DESCRIPTION: SEQ ID NO:9:

Thr Ser Gln Tyr Arg Gly Val Thr Arg His Arg Trp Thr Gly Arg Tyr
1               5                  10                  15

Glu Ala His Leu Trp Asp Asn Ser Phe Lys Lys Glu Gly His Ser Arg
                20                  25                  30

Lys Gly Arg Gln Val Tyr Leu Gly Gly Tyr Asp Met Glu Glu Lys Ala
            35                  40                  45

Ala Arg Ala Tyr Asp Leu Ala Ala Leu Lys Tyr Trp Gly Pro Ser Thr
        50                  55                  60

His Thr Asn Phe Ser Ala Glu Asn Tyr Gln Lys Glu Ile
65                  70                  75

(2) INFORMATION FOR SEQ ID NO:10:

(i) SEQUENCE CHARACTERISTICS:
         (A) LENGTH: 69 amino acids
         (B) TYPE: amino acid
         (C) STRANDEDNESS:
         (D) TOPOLOGY: linear
```

(ii) MOLECULE TYPE: peptide (ix) FEATURE:
    (A) NAME/KEY: Peptide
    (B) LOCATION: 1..69
    (D) OTHER INFORMATION: /note= "ANT-R2 direct repeat"

(ix) FEATURE:
    (A) NAME/KEY: Region
    (B) LOCATION: 37..51
    (D) OTHER INFORMATION: /note= "putative ANT-R2 amphipathic alpha-helix"

(xi) SEQUENCE DESCRIPTION: SEQ ID NO:10:

```
Ala Ser Ile Tyr Arg Gly Val Thr Arg His His Gln His Gly Arg Trp
1               5                   10                  15

Gln Ala Arg Ile Gly Arg Val Ala Gly Asn Lys Asp Leu Tyr Leu Gly
            20                  25                  30

Thr Phe Gly Thr Gln Glu Glu Ala Ala Glu Ala Tyr Asp Val Ala Ala
        35                  40                  45

Ile Lys Phe Arg Gly Thr Asn Ala Val Thr Asn Phe Asp Ile Thr Arg
    50                  55                  60

Tyr Asp Val Asp Arg
65
```

(2) INFORMATION FOR SEQ ID NO:11:

(i) SEQUENCE CHARACTERISTICS:
        (A) LENGTH: 67 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..67
        (D) OTHER INFORMATION: /note= "RAP2.7-R1 direct repeat"

(ix) FEATURE:
        (A) NAME/KEY: Region
        (B) LOCATION: 33..49
        (D) OTHER INFORMATION: /note= "putative RAP2.7-R1 amphipathic alpha helix (SEQ ID NO:36)"

(xi) SEQUENCE DESCRIPTION: SEQ ID NO:11:

```
Ser Ser Gln Tyr Arg Gly Val Thr Phe Tyr Arg Arg Thr Gly Arg Trp
1               5                   10                  15

Glu Ser His Ile Trp Asp Cys Gly Lys Gln Val Tyr Leu Gly Gly Phe
            20                  25                  30

Asp Thr Ala His Ala Ala Ala Arg Ala Tyr Asp Arg Ala Ala Ile Lys
        35                  40                  45

Phe Arg Gly Val Asp Ala Asp Ile Asn Phe Thr Leu Gly Asp Tyr Glu
    50                  55                  60

Glu Asp Met
65
```

(2) INFORMATION FOR SEQ ID NO:12:

(i) SEQUENCE CHARACTERISTICS:
        (A) LENGTH: 53 amino acids
        (B) TYPE: amino acid
        (C) STRANDEDNESS:
        (D) TOPOLOGY: linear

```
    (ii) MOLECULE TYPE: peptide (ix) FEATURE:
         (A) NAME/KEY: Peptide
         (B) LOCATION: 1..53
         (D) OTHER INFORMATION: /note= "RAP2.7-R2 direct repeat"

(ix) FEATURE:
         (A) NAME/KEY: Region
         (B) LOCATION: 26..34
         (D) OTHER INFORMATION: /note= "putative RAP2.7-R2
             amphipathic alpha-helix"

(xi) SEQUENCE DESCRIPTION: SEQ ID NO:12:

Ser Ser Lys Tyr Arg Gly Val Thr Leu His Lys Cys Gly Arg Trp Glu
1               5                   10                  15

Ala Arg Met Gly Gln Phe Leu Gly Lys Lys Ala Tyr Asp Lys Ala Ala
            20                  25                  30

Ile Asn Thr Asn Gly Arg Glu Ala Val Thr Asn Phe Glu Met Ser Ser
                35                  40                  45

Tyr Gln Asn Glu Ile
        50

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Tyr Arg Gly Val Thr
1               5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 5
         (D) OTHER INFORMATION: /product= "OTHER"
             /note= "Xaa = Ala or Ser"

(ix) FEATURE:
         (A) NAME/KEY: Modified-site
         (B) LOCATION: 6
         (D) OTHER INFORMATION: /product= "OTHER"
             /note= "Xaa = Arg or His"

(xi) SEQUENCE DESCRIPTION: SEQ ID NO:14:

Gly Arg Trp Glu Xaa Xaa
1               5

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:15:

Val Tyr Leu Gly
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Ala Ala Ile Lys
1

(2) INFORMATION FOR SEQ ID NO:17:

(i) SEQUENCE CHARACTERISTICS:
        (A) LENGTH: 69 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..69
        (D) OTHER INFORMATION: /note= "AP2 domain within tobacco
            EREBP-1"

(ix) FEATURE:
        (A) NAME/KEY: Region
        (B) LOCATION: 36..51
        (D) OTHER INFORMATION: /note= "putative EREBP-1
            amphipathic alpha-helix"

(xi) SEQUENCE DESCRIPTION: SEQ ID NO:17:

Gly Arg His Tyr Arg Gly Val Arg Arg Arg Pro Trp Gly Lys Phe Ala
1               5                   10                  15

Ala Glu Ile Arg Asp Pro Ala Lys Asn Gly Ala Arg Val Trp Leu Gly
            20                  25                  30

Thr Tyr Glu Thr Asp Glu Glu Ala Ala Ile Ala Tyr Asp Lys Ala Ala
        35                  40                  45

Tyr Arg Met Arg Gly Ser Lys Ala His Leu Asn Phe Pro Leu Glu Val
    50                  55                  60

Ala Asn Phe Lys Gln
65

(2) INFORMATION FOR SEQ ID NO:18:

(i) SEQUENCE CHARACTERISTICS:
        (A) LENGTH: 69 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..69
        (D) OTHER INFORMATION: /note= "AP2 domain within tobacco -continued

```
            EREBP-2"

(ix) FEATURE:
        (A) NAME/KEY: Region
        (B) LOCATION: 35..51
        (D) OTHER INFORMATION: /note= "putative EREBP-2
            amphipathic alpha-helix"

(xi) SEQUENCE DESCRIPTION: SEQ ID NO:18:

Gly Arg His Tyr Arg Gly Val Arg Gln Arg Pro Trp Gly Lys Phe Ala
1               5                   10                  15

Ala Glu Ile Arg Asp Pro Ala Lys Asn Gly Ala Arg Val Trp Leu Gly
            20                  25                  30

Thr Tyr Glu Thr Ala Glu Glu Ala Ala Leu Ala Tyr Asp Lys Ala Ala
        35                  40                  45

Tyr Arg Met Arg Gly Ser Lys Ala Leu Leu Asn Phe Pro His Arg Ile
    50                  55                  60

Gly Leu Asn Glu Pro
65

(2) INFORMATION FOR SEQ ID NO:19:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "AP2 domain within tobacco
            EREBP-3"

(ix) FEATURE:
        (A) NAME/KEY: Region
        (B) LOCATION: 35..50
        (D) OTHER INFORMATION: /note= "putative EREBP-3 amphipathic
            alpha-helix (SEQ ID NO:41)"

(xi) SEQUENCE DESCRIPTION: SEQ ID NO:19:

Glu Val His Tyr Arg Gly Val Arg Lys Arg Pro Trp Gly Arg Tyr Ala
1               5                   10                  15

Ala Glu Ile Arg Asp Pro Gly Lys Lys Ser Arg Val Trp Leu Gly Thr
            20                  25                  30

Phe Asp Thr Ala Glu Glu Ala Ala Lys Ala Tyr Asp Thr Ala Ala Arg
        35                  40                  45

Glu Phe Arg Gly Pro Lys Ala Lys Thr Asn Phe Pro Ser Pro Thr Glu
    50                  55                  60

Asn Gln Ser Pro
65

(2) INFORMATION FOR SEQ ID NO:20:

(i) SEQUENCE CHARACTERISTICS:
        (A) LENGTH: 69 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..69
```

(D) OTHER INFORMATION: /note= "AP2 domain within tobacco
            EREBP-4"

(ix) FEATURE:
        (A) NAME/KEY: Region
        (B) LOCATION: 35..51
        (D) OTHER INFORMATION: /note= "putative EREBP-4
            amphipathic alpha-helix"

(xi) SEQUENCE DESCRIPTION: SEQ ID NO:20:

Lys Lys His Tyr Arg Gly Val Arg Gln Arg Pro Trp Gly Lys Phe Ala
1               5                   10                  15

Ala Glu Ile Arg Asp Pro Asn Arg Lys Gly Thr Arg Val Trp Leu Gly
            20                  25                  30

Thr Phe Asp Thr Ala Ile Glu Ala Ala Lys Ala Tyr Asp Arg Ala Ala
        35                  40                  45

Phe Lys Leu Arg Gly Ser Lys Ala Ile Val Asn Phe Pro His Arg Ile
    50                  55                  60

Gly Leu Asn Glu Pro
65

(2) INFORMATION FOR SEQ ID NO:21:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "EREBP-like Arabidopsis
            RAP2.2 AP2 domain"

(ix) FEATURE:
        (A) NAME/KEY: Region
        (B) LOCATION: 34..51
        (D) OTHER INFORMATION: /note= "putative RAP2.2 amphipathic
            alpha-helix (SEQ ID NO:38)"

(xi) SEQUENCE DESCRIPTION: SEQ ID NO:21:

Lys Asn Gln Tyr Arg Gly Ile Arg Gln Arg Pro Trp Gly Lys Trp Ala
1               5                   10                  15

Ala Glu Ile Arg Asp Pro Arg Lys Gly Ser Arg Glu Trp Leu Gly Thr
            20                  25                  30

Phe Asp Thr Ala Glu Glu Ala Ala Arg Ala Tyr Asp Ala Ala Ala Arg
        35                  40                  45

Arg Ile Arg Gly Thr Lys Ala Lys Val Asn Phe Pro Glu Glu Lys Asn
    50                  55                  60

Pro Ser Val Val
65

(2) INFORMATION FOR SEQ ID NO:22:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide (B) LOCATION: 1..68
        (D) OTHER INFORMATION: /note= "EREBP-like Arabidopsis
            RAP2.3 AP2 domain"

(ix) FEATURE:
        (A) NAME/KEY: Region
        (B) LOCATION: 36..50
        (D) OTHER INFORMATION: /note= "putative RAP2.3 amphipathic
            alpha-helix"

(xi) SEQUENCE DESCRIPTION: SEQ ID NO:22:

Lys Asn Val Tyr Arg Gly Ile Arg Lys Arg Pro Trp Gly Lys Trp Ala
1               5                   10                  15

Ala Glu Ile Arg Asp Pro Arg Lys Gly Val Arg Val Trp Leu Gly Thr
            20                  25                  30

Phe Asn Thr Ala Glu Glu Ala Ala Met Ala Tyr Asp Val Ala Ala Lys
        35                  40                  45

Gln Ile Arg Gly Asp Lys Ala Lys Leu Asn Phe Pro Asp Leu His His
    50                  55                  60

Pro Pro Pro Pro
65

(2) INFORMATION FOR SEQ ID NO:23:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "EREBP-like Arabidopsis
            RAP2.5 AP2 domain"

(ix) FEATURE:
        (A) NAME/KEY: Region
        (B) LOCATION: 35..50
        (D) OTHER INFORMATION: /note= "putative RAP2.5 amphipathic
            alpha-helix (SEQ ID NO:39)"

(xi) SEQUENCE DESCRIPTION: SEQ ID NO:23:

Glu Ile Arg Tyr Arg Gly Val Arg Lys Arg Pro Trp Gly Arg Tyr Ala
1               5                   10                  15

Ala Glu Ile Arg Asp Pro Gly Lys Lys Thr Arg Val Trp Leu Gly Thr
            20                  25                  30

Phe Asp Thr Ala Glu Glu Ala Ala Arg Ala Tyr Asp Thr Ala Ala Arg
        35                  40                  45

Asp Phe Arg Gly Ala Lys Ala Lys Thr Asn Phe Pro Thr Phe Leu Glu
    50                  55                  60

Leu Ser Asp Gln
65

(2) INFORMATION FOR SEQ ID NO:24:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:

(A) NAME/KEY: Peptide
(B) LOCATION: 1..68
(D) OTHER INFORMATION: /note= "EREBP-like Arabidopsis RAP2.6 AP2 domain"

(ix) FEATURE:
(A) NAME/KEY: Region
(B) LOCATION: 34..51
(D) OTHER INFORMATION: /note= "putative RAP2.6 amphipathic alpha-helix"

(xi) SEQUENCE DESCRIPTION: SEQ ID NO:24:

```
Pro Lys Lys Tyr Arg Gly Val Arg Gln Arg Pro Trp Gly Lys Trp Ala
1               5                  10                 15

Ala Glu Ile Arg Asp Pro His Lys Ala Thr Arg Val Trp Leu Gly Thr
            20                 25                 30

Phe Glu Thr Ala Glu Ala Ala Arg Ala Tyr Asp Ala Ala Ala Leu
        35                 40                 45

Arg Phe Arg Gly Ser Lys Ala Lys Leu Asn Phe Pro Glu Asn Val Gly
50                  55                 60

Thr Gln Thr Ile
65
```

(2) INFORMATION FOR SEQ ID NO:25:

(i) SEQUENCE CHARACTERISTICS:
(A) LENGTH: 68 amino acids
(B) TYPE: amino acid
(C) STRANDEDNESS:
(D) TOPOLOGY: linear (ii) MOLECULE TYPE: peptide (ix) FEATURE:
(A) NAME/KEY: Peptide
(B) LOCATION: 1..68
(D) OTHER INFORMATION: /note= "EREBP-like Arabidopsis RAP2.12 AP2 domain"

(ix) FEATURE:
(A) NAME/KEY: Region
(B) LOCATION: 34..51
(D) OTHER INFORMATION: /note= "putative RAP2.12 amphipathic alpha-helix (SEQ ID NO:40)"

(xi) SEQUENCE DESCRIPTION: SEQ ID NO:25:

```
Lys Asn Gln Tyr Arg Gly Ile Arg Gln Arg Pro Trp Gly Lys Trp Ala
1               5                  10                 15

Ala Glu Ile Arg Asp Pro Arg Glu Gly Ala Arg Ile Trp Leu Gly Thr
            20                 25                 30

Phe Lys Thr Ala Glu Glu Ala Ala Arg Ala Tyr Asp Ala Ala Ala Arg
        35                 40                 45

Arg Ile Arg Gly Ser Lys Ala Lys Val Asn Phe Pro Glu Glu Asn Met
50                  55                 60

Lys Ala Asn Ser
65
```

(2) INFORMATION FOR SEQ ID NO:26:

(i) SEQUENCE CHARACTERISTICS:
(A) LENGTH: 68 amino acids
(B) TYPE: amino acid
(C) STRANDEDNESS:
(D) TOPOLOGY: linear (ii) MOLECULE TYPE: peptide

```
        (ix) FEATURE:
             (A) NAME/KEY: Peptide
             (B) LOCATION: 1..68
             (D) OTHER INFORMATION: /note= "EREBP-like Arabidopsis TINY
                 AP2 domain"

(ix) FEATURE:
             (A) NAME/KEY: Region
             (B) LOCATION: 35..50
             (D) OTHER INFORMATION: /note= "putative TINY amphipathic
                 alpha-helix"

(xi) SEQUENCE DESCRIPTION: SEQ ID NO:26:

His Pro Val Tyr Arg Gly Val Arg Lys Arg Asn Trp Gly Lys Trp Val
1               5                   10                  15

Ser Glu Ile Arg Glu Pro Arg Lys Lys Ser Arg Ile Trp Leu Gly Thr
            20                  25                  30

Phe Pro Ser Pro Glu Met Ala Ala Arg Ala His Asp Val Ala Ala Leu
        35                  40                  45

Ser Ile Lys Gly Ala Ser Ala Ile Leu Asn Phe Pro Asp Leu Ala Gly
    50                  55                  60

Ser Phe Pro Arg
65

(2) INFORMATION FOR SEQ ID NO:27:

(i) SEQUENCE CHARACTERISTICS:
             (A) LENGTH: 68 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Peptide
             (B) LOCATION: 1..68
             (D) OTHER INFORMATION: /note= "EREBP-like Arabidopsis
                 RAP2.1 AP2 domain"

(ix) FEATURE:
             (A) NAME/KEY: Region
             (B) LOCATION: 35..50
             (D) OTHER INFORMATION: /note= "putative RAP2.1 amphipathic
                 alpha-helix"

(xi) SEQUENCE DESCRIPTION: SEQ ID NO:27:

Arg Lys Pro Tyr Arg Gly Ile Arg Arg Arg Lys Trp Gly Lys Trp Val
1               5                   10                  15

Ala Glu Ile Arg Glu Pro Asn Lys Arg Ser Arg Leu Trp Leu Gly Ser
            20                  25                  30

Tyr Thr Thr Asp Ile Ala Ala Ala Arg Ala Tyr Asp Val Ala Val Phe
        35                  40                  45

Tyr Leu Arg Gly Pro Ser Ala Arg Leu Asn Phe Pro Asp Leu Leu Leu
    50                  55                  60

Gln Glu Glu Asp
65

(2) INFORMATION FOR SEQ ID NO:28:

(i) SEQUENCE CHARACTERISTICS:
             (A) LENGTH: 68 amino acids
             (B) TYPE: amino acid
             (C) STRANDEDNESS:
             (D) TOPOLOGY: linear (ii) MOLECULE TYPE: peptide
```

```
        (ix) FEATURE:
              (A) NAME/KEY: Peptide
              (B) LOCATION: 1..68
              (D) OTHER INFORMATION: /note= "EREBP-like Arabidopsis
                   RAP2.4 AP2 domain"

(ix) FEATURE:
              (A) NAME/KEY: Region
              (B) LOCATION: 35..50
              (D) OTHER INFORMATION: /note= "putative RAP2.4 amphipathic
                   alpha-helix"

(xi) SEQUENCE DESCRIPTION: SEQ ID NO:28:

Thr Lys Leu Tyr Arg Gly Val Arg Gln Arg His Trp Gly Lys Trp Val
1               5                   10                  15

Ala Glu Ile Arg Leu Pro Arg Asn Arg Thr Arg Leu Trp Leu Gly Thr
            20                  25                  30

Phe Asp Thr Ala Glu Glu Ala Ala Leu Ala Tyr Asp Lys Ala Ala Tyr
        35                  40                  45

Lys Leu Arg Gly Asp Phe Ala Arg Leu Asn Phe Pro Asn Leu Arg His
    50                  55                  60

Asn Gly Phe His
65

(2) INFORMATION FOR SEQ ID NO:29:

(i) SEQUENCE CHARACTERISTICS:
              (A) LENGTH: 66 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Peptide
              (B) LOCATION: 1..66
              (D) OTHER INFORMATION: /note= "EREBP-like Arabidopsis
                   RAP2.8 AP2 domain"

(ix) FEATURE:
              (A) NAME/KEY: Region
              (B) LOCATION: 33..48
              (D) OTHER INFORMATION: /note= "putative RAP2.8 amphipathic
                   alpha-helix"

(xi) SEQUENCE DESCRIPTION: SEQ ID NO:29:

Ser Ser Lys Tyr Lys Gly Val Val Pro Gln Pro Asn Gly Arg Trp Gly
1               5                   10                  15

Ala Gln Ile Tyr Glu Lys His Gln Arg Val Trp Leu Gly Thr Phe Asn
            20                  25                  30

Glu Gln Glu Glu Ala Ala Arg Ser Tyr Asp Ile Ala Ala Cys Arg Phe
        35                  40                  45

Arg Gly Arg Asp Ala Val Val Asn Phe Lys Asn Val Leu Glu Asp Gly
    50                  55                  60

Asp Leu
65

(2) INFORMATION FOR SEQ ID NO:30:

(i) SEQUENCE CHARACTERISTICS:
              (A) LENGTH: 68 amino acids
              (B) TYPE: amino acid
              (C) STRANDEDNESS:
              (D) TOPOLOGY: linear
```

```
        (ii) MOLECULE TYPE: peptide (ix) FEATURE:
             (A) NAME/KEY: Peptide
             (B) LOCATION: 1..68
             (D) OTHER INFORMATION: /note= "EREBP-like Arabidopsis
                 RAP2.10 AP2 domain"

(ix) FEATURE:
             (A) NAME/KEY: Region
             (B) LOCATION: 36..51
             (D) OTHER INFORMATION: /note= "putative RAP2.10
                 amphipathic alpha-helix"

(xi) SEQUENCE DESCRIPTION: SEQ ID NO:30:

Asp Lys Pro Tyr Lys Gly Ile Arg Met Arg Lys Trp Gly Lys Trp Val
1               5                   10                  15

Ala Glu Ile Arg Glu Pro Asn Lys Arg Ser Arg Ile Trp Leu Gly Ser
            20                  25                  30

Tyr Ser Thr Pro Glu Ala Ala Ala Arg Ala Tyr Asp Thr Ala Val Phe
        35                  40                  45

Tyr Leu Arg Gly Pro Ser Ala Arg Leu Asn Phe Pro Glu Leu Leu Ala
50                  55                  60

Gly Val Thr Val
65

(2) INFORMATION FOR SEQ ID NO:31:

(i) SEQUENCE CHARACTERISTICS:
            (A) LENGTH: 68 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: Peptide
             (B) LOCATION: 1..68
             (D) OTHER INFORMATION: /note= "EREBP-like Arabidopsis
                 RAP2.11 AP2 domain"

(ix) FEATURE:
             (A) NAME/KEY: Region
             (B) LOCATION: 34..50
             (D) OTHER INFORMATION: /note= "putative RAP2.11
                 amphipathic alpha-helix"

(xi) SEQUENCE DESCRIPTION: SEQ ID NO:31:

Lys Thr Lys Phe Val Gly Val Arg Gln Arg Pro Ser Gly Lys Trp Val
1               5                   10                  15

Ala Glu Ile Lys Asp Thr Thr Gln Lys Ile Arg Met Trp Leu Gly Thr
            20                  25                  30

Phe Glu Thr Ala Glu Glu Ala Ala Arg Ala Tyr Asp Glu Ala Ala Cys
        35                  40                  45

Leu Leu Arg Gly Ser Asn Thr Arg Thr Asn Phe Ala Asn His Phe Pro
50                  55                  60

Asn Asn Ser Gln
65

(2) INFORMATION FOR SEQ ID NO:32:

(i) SEQUENCE CHARACTERISTICS:
            (A) LENGTH: 5 amino acids
            (B) TYPE: amino acid
            (C) STRANDEDNESS:
            (D) TOPOLOGY: linear
```

(ii) MOLECULE TYPE: peptide (ix) FEATURE:
            (A) NAME/KEY: Modified-site
            (B) LOCATION: 4
            (D) OTHER INFORMATION: /product= "OTHER"
                /note= "Xaa = Val or Ile"

(xi) SEQUENCE DESCRIPTION: SEQ ID NO:32:

Tyr Arg Gly Xaa Arg
1               5

(2) INFORMATION FOR SEQ ID NO:33:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /note= "Xaa = positively charged
                amino acid"

(ix) FEATURE:
            (A) NAME/KEY: Modified-site
            (B) LOCATION: 4
            (D) OTHER INFORMATION: /product= "OTHER"
                /note= "Xaa = Trp, Phe or Tyr"

(ix) FEATURE:
            (A) NAME/KEY: Modified-site
            (B) LOCATION: 5
            (D) OTHER INFORMATION: /product= "OTHER"
                /note= "Xaa = Ala or Val"

(ix) FEATURE:
            (A) NAME/KEY: Modified-site
            (B) LOCATION: 9
            (D) OTHER INFORMATION: /product= "OTHER"
                /note= "Xaa = Arg or Lys"

(ix) FEATURE:
            (A) NAME/KEY: Modified-site
            (B) LOCATION: 10
            (D) OTHER INFORMATION: /product= "OTHER"
                /note= "Xaa = Asp or Glu"

(xi) SEQUENCE DESCRIPTION: SEQ ID NO:33:

Trp Gly Xaa Xaa Xaa Ala Glu Ile Xaa Xaa
1               5                   10

(2) INFORMATION FOR SEQ ID NO:34:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "OTHER"
                /note= "Xaa = Ser or Thr"

(ix) FEATURE:

```
            (A) NAME/KEY: Modified-site
            (B) LOCATION: 5
            (D) OTHER INFORMATION: /product= "OTHER"
                /note= "Xaa = Tyr or Phe"

(xi) SEQUENCE DESCRIPTION: SEQ ID NO:34:

Trp Leu Gly Xaa Xaa
1               5

(2) INFORMATION FOR SEQ ID NO:35:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /product= "OTHER"
                /note= "Xaa = Ile, Leu or positively
                charged amino acid"

(xi) SEQUENCE DESCRIPTION: SEQ ID NO:35:

Glu Glu Ala Ala Xaa Ala Tyr Asp
1               5

(2) INFORMATION FOR SEQ ID NO:36:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..17
            (D) OTHER INFORMATION: /note= "putative RAP2.7-R1
                amphipathic alpha-helix"

(xi) SEQUENCE DESCRIPTION: SEQ ID NO:36:

Asp Thr Ala His Ala Ala Ala Arg Ala Tyr Asp Arg Ala Ala Ile Lys
1               5                   10                  15

Phe (2) INFORMATION FOR SEQ ID NO:37:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..16
            (D) OTHER INFORMATION: /note= "putative ANT-R1 amphipathic
                alpha-helix"

(xi) SEQUENCE DESCRIPTION: SEQ ID NO:37:

Met Glu Glu Lys Ala Ala Arg Ala Tyr Asp Leu Ala Ala Leu Lys Tyr
1               5                   10                  15
```

(2) INFORMATION FOR SEQ ID NO:38:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..18
        (D) OTHER INFORMATION: /note= "putative RAP2.2 amphipathic
            alpha-helix"

(xi) SEQUENCE DESCRIPTION: SEQ ID NO:38:

Asp Thr Ala Glu Glu Ala Ala Arg Ala Tyr Asp Ala Ala Ala Arg Arg
1               5                   10                  15

Ile Arg (2) INFORMATION FOR SEQ ID NO:39:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "putative RAP2.5 amphipathic
            alpha-helix"

(xi) SEQUENCE DESCRIPTION: SEQ ID NO:39:

Thr Ala Glu Glu Ala Ala Arg Ala Tyr Asp Thr Ala Ala Arg Asp Phe
1               5                   10                  15

(2) INFORMATION FOR SEQ ID NO:40:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..18
        (D) OTHER INFORMATION: /note= "putative RAP2.12
            amphipathic alpha-helix"

(xi) SEQUENCE DESCRIPTION: SEQ ID NO:40:

Lys Thr Ala Glu Glu Ala Ala Arg Ala Tyr Asp Ala Ala Ala Arg Arg
1               5                   10                  15

Ile Arg (2) INFORMATION FOR SEQ ID NO:41:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "putative EREBP-3
            amphipathic alpha-helix"

(xi) SEQUENCE DESCRIPTION: SEQ ID NO:41:

Thr Ala Glu Glu Ala Ala Lys Ala Tyr Asp Thr Ala Ala Arg Glu Phe
1               5                   10                  15

(2) INFORMATION FOR SEQ ID NO:42:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..25
        (D) OTHER INFORMATION: /note= "AP2 linker region"

(xi) SEQUENCE DESCRIPTION: SEQ ID NO:42:

Lys Gln Met Thr Asn Leu Thr Lys Glu Glu Phe Val His Val Leu Arg
1               5                   10                  15

Arg Gln Ser Thr Gly Phe Pro Arg Gly
            20                  25

(2) INFORMATION FOR SEQ ID NO:43:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..26
        (D) OTHER INFORMATION: /note= "ANT linker region"

(xi) SEQUENCE DESCRIPTION: SEQ ID NO:43:

Glu Asp Met Met Lys Asn Met Thr Arg Gln Glu Tyr Val Ala His Leu
1               5                   10                  15

Arg Arg Lys Ser Ser Gly Phe Ser Arg Gly
            20                  25

(2) INFORMATION FOR SEQ ID NO:44:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..26
        (D) OTHER INFORMATION: /note= "RAP2.7 linker region"

(xi) SEQUENCE DESCRIPTION: SEQ ID NO:44:

```
Met Lys Gln Val Gln Asn Leu Ser Lys Glu Glu Phe Val His Ile Leu
1               5                  10                 15

Arg Arg Gln Ser Thr Gly Phe Ser Arg Gly
            20                  25
```

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = positively charged
            amino acid"

(xi) SEQUENCE DESCRIPTION: SEQ ID NO:45:

```
Asn Leu Thr Xaa Glu Glu Phe Val His
1               5
```

(2) INFORMATION FOR SEQ ID NO:46:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

```
Leu Arg Arg Gln Ser Thr Gly Phe Ser Arg Gly
1               5                  10
```

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "JOAP2U primer"

(xi) SEQUENCE DESCRIPTION: SEQ ID NO:47:

```
GTTGCCGCTG CCGTAGTG                                              18
```

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22

-continued

```
            (D) OTHER INFORMATION: /note= "JOAP2L primer"

(xi) SEQUENCE DESCRIPTION: SEQ ID NO:48:

GGTTCATCCT GAGCCGCATA TC                                              22

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..24
            (D) OTHER INFORMATION: /note= "JORAP2.1U primer"

(xi) SEQUENCE DESCRIPTION: SEQ ID NO:49:

CTCAAGAAGA AGTGCCTAAC CACG                                            24

(2) INFORMATION FOR SEQ ID NO:50:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "JORAP2.1L primer"

(xi) SEQUENCE DESCRIPTION: SEQ ID NO:50:

GCAGAAGCTA GAAGAGCGTC GA                                              22

(2) INFORMATION FOR SEQ ID NO:51:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "JORAP2.2U primer"

(xi) SEQUENCE DESCRIPTION: SEQ ID NO:51:

GGAAAATGGG CTGCGGAG                                                   18

(2) INFORMATION FOR SEQ ID NO:52:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
```

(B) LOCATION: 1..22
            (D) OTHER INFORMATION: /note= "JORAP2.2L primer"

(xi) SEQUENCE DESCRIPTION: SEQ ID NO:52:

GTTACCTCCA GCATCGAACG AG                                        22

(2) INFORMATION FOR SEQ ID NO:53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "JORAP2.4U primer"

(xi) SEQUENCE DESCRIPTION: SEQ ID NO:53:

GCTGGATCTT GTTTCGCTTA CG                                        22

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "JORAP2.4L primer"

(xi) SEQUENCE DESCRIPTION: SEQ ID NO:54:

GCTTCAAGCT TAGCGTCGAC TG                                        22

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "JORAP2.5U primer"

(xi) SEQUENCE DESCRIPTION: SEQ ID NO:55:

AGATGGGCTT GAAACCCGAC                                           20

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:

```
        (A) NAME/KEY: -
        (B) LOCATION: 1..18
        (D) OTHER INFORMATION: /note= "JORAP2.5L primer"

(xi) SEQUENCE DESCRIPTION: SEQ ID NO:56:

CTGGCTAGGG CTACGCGC                                                    18

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "JORAP2.6U primer"

(xi) SEQUENCE DESCRIPTION: SEQ ID NO:57:

TTCTTTGCCT CCTCAACCAT TG                                               22

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "JORAP2.6L primer"

(xi) SEQUENCE DESCRIPTION: SEQ ID NO:58:

TCTGAGTTCC AACATTTTCG GG                                               22

(2) INFORMATION FOR SEQ ID NO:59:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "JORAP2.7U primer"

(xi) SEQUENCE DESCRIPTION: SEQ ID NO:59:

GAAATTGGTA ACTCCGGTTC CG                                               22

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA
```

```
    (ix) FEATURE:
         (A) NAME/KEY: -
         (B) LOCATION: 1..22
         (D) OTHER INFORMATION: /note= "JORAP2.7L primer"

(xi) SEQUENCE DESCRIPTION: SEQ ID NO:60:

CCATTTTGCT TTGGCGCATT AC                                                    22

(2) INFORMATION FOR SEQ ID NO:61:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..19
         (D) OTHER INFORMATION: /note= "JORAP2.8U primer"

(xi) SEQUENCE DESCRIPTION: SEQ ID NO:61:

GGCGTTACGC CTCTACCGG                                                        19

(2) INFORMATION FOR SEQ ID NO:62:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..20
         (D) OTHER INFORMATION: /note= "JORAP2.8L primer"

(xi) SEQUENCE DESCRIPTION: SEQ ID NO:62:

CGCCGTCTTC CAGAACGTTC                                                       20

(2) INFORMATION FOR SEQ ID NO:63:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..21
         (D) OTHER INFORMATION: /note= "JORAP2.9U primer"

(xi) SEQUENCE DESCRIPTION: SEQ ID NO:63:

ATCACGGATC TGGCTTGGTT C                                                     21

(2) INFORMATION FOR SEQ ID NO:64:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA
```

```
        (ix) FEATURE:
              (A) NAME/KEY: -
              (B) LOCATION: 1..22
              (D) OTHER INFORMATION: /note= "JORAP2.9L primer"

(xi) SEQUENCE DESCRIPTION: SEQ ID NO:64:

GCCTTCTTCC GTATCAACGT CG                                                   22

(2) INFORMATION FOR SEQ ID NO:65:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..19
              (D) OTHER INFORMATION: /note= "JORAP2.10U primer"

(xi) SEQUENCE DESCRIPTION: SEQ ID NO:65:

GTCAACTCCG GCGGTTACG                                                       19

(2) INFORMATION FOR SEQ ID NO:66:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..21
              (D) OTHER INFORMATION: /note= "JORAP2.10L primer"

(xi) SEQUENCE DESCRIPTION: SEQ ID NO:66:

TCTCCTTATA TACGCCGCCG A                                                    21

(2) INFORMATION FOR SEQ ID NO:67:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..23
              (D) OTHER INFORMATION: /note= "JORAP2.11U primer"

(xi) SEQUENCE DESCRIPTION: SEQ ID NO:67:

GAGAAGAGCA AAGGCAACAA GAC                                                  23

(2) INFORMATION FOR SEQ ID NO:68:

(i) SEQUENCE CHARACTERISTICS:
              (A) LENGTH: 23 base pairs
              (B) TYPE: nucleic acid
              (C) STRANDEDNESS: single
              (D) TOPOLOGY: linear
```

(ii) MOLECULE TYPE: DNA (ix) FEATURE:
            (A) NAME/KEY: -
            (B) LOCATION: 1..23
            (D) OTHER INFORMATION: /note= "JORAP2.11L primer"

(xi) SEQUENCE DESCRIPTION: SEQ ID NO:68:

AGTTGTTAGG AAAATGGTTT GCG                                              23

(2) INFORMATION FOR SEQ ID NO:69:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..25
            (D) OTHER INFORMATION: /note= "JORAP2.12U primer"

(xi) SEQUENCE DESCRIPTION: SEQ ID NO:69:

AAACCATTCG TTTTCACTTC GACTC                                            25

(2) INFORMATION FOR SEQ ID NO:70:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..25
            (D) OTHER INFORMATION: /note= "JORAP2.12L primer"

(xi) SEQUENCE DESCRIPTION: SEQ ID NO:70:

TCACAGAGCG TTTCTGAGAA TTAGC                                            25

(2) INFORMATION FOR SEQ ID NO:71:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "AP2U primer"

(xi) SEQUENCE DESCRIPTION: SEQ ID NO:71:

ATGTGGGATC TAAACGACGC AC                                               22

(2) INFORMATION FOR SEQ ID NO:72:

(i) SEQUENCE CHARACTERISTICS:
            (A) LENGTH: 19 base pairs
            (B) TYPE: nucleic acid
            (C) STRANDEDNESS: single
            (D) TOPOLOGY: linear -continued (ii) MOLECULE TYPE: DNA (ix) FEATURE:
        (A) NAME/KEY: -
        (B) LOCATION: 1..19
        (D) OTHER INFORMATION: /note= "AP2L primer"

(xi) SEQUENCE DESCRIPTION: SEQ ID NO:72:

GATCTTGGTC CACGCCGAC                                                     19

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.1U primer"

(xi) SEQUENCE DESCRIPTION: SEQ ID NO:73:

AAGAGGACCA TCTCTCAG                                                      18

(2) INFORMATION FOR SEQ ID NO:74:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.1L primer"

(xi) SEQUENCE DESCRIPTION: SEQ ID NO:74:

AACACTCGCT AGCTTCTC                                                      18

(2) INFORMATION FOR SEQ ID NO:75:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.2U primer"

(xi) SEQUENCE DESCRIPTION: SEQ ID NO:75:

TGGTTCAGCA GCCAACAC                                                      18

(2) INFORMATION FOR SEQ ID NO:76:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "RAP2.2L primer"

(xi) SEQUENCE DESCRIPTION: SEQ ID NO:76:

CAATGCATAG AGCTTGAGG                                              19

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.4U primer"

(xi) SEQUENCE DESCRIPTION: SEQ ID NO:77:

ACGGATTTCA CATCGGAG                                               18

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "RAP2.4L primer"

(xi) SEQUENCE DESCRIPTION: SEQ ID NO:78:

CTAAGCTAGA ATCGAATCC                                              19

(2) INFORMATION FOR SEQ ID NO:79:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.5U primer"

(xi) SEQUENCE DESCRIPTION: SEQ ID NO:79:

TACCGGTTTC GCGCGTAG                                               18

(2) INFORMATION FOR SEQ ID NO:80:

(i) SEQUENCE CHARACTERISTICS:
        (A) LENGTH: 21 base pairs
        (B) TYPE: nucleic acid

```
            (C) STRANDEDNESS: single
            (D) TOPOLOGY: linear (ii) MOLECULE TYPE: DNA (ix) FEATURE:
            (A) NAME/KEY: -
            (B) LOCATION: 1..21
            (D) OTHER INFORMATION: /note= "RAP2.5L primer"

(xi) SEQUENCE DESCRIPTION: SEQ ID NO:80:

CACCTTCGAA ATCAACGACC G                                              21

(2) INFORMATION FOR SEQ ID NO:81:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "RAP2.6U primer"

(xi) SEQUENCE DESCRIPTION: SEQ ID NO:81:

TTCCCCGAAA ATGTTGGAAC TC                                             22

(2) INFORMATION FOR SEQ ID NO:82:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..25
            (D) OTHER INFORMATION: /note= "RAP2.6L primer"

(xi) SEQUENCE DESCRIPTION: SEQ ID NO:82:

TGGGAGAGAA AAAATTGGTA GATCG                                          25

(2) INFORMATION FOR SEQ ID NO:83:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "RAP2.7U primer"

(xi) SEQUENCE DESCRIPTION: SEQ ID NO:83:

CGATGGAGAC GAAGACTC                                                  18

(2) INFORMATION FOR SEQ ID NO:84:

(i) SEQUENCE CHARACTERISTICS:
            (A) LENGTH: 18 base pairs
```

```
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "RAP2.7L primer"

(xi) SEQUENCE DESCRIPTION: SEQ ID NO:84:

GTCGGAACCG GAGTTACC                                                    18

(2) INFORMATION FOR SEQ ID NO:85:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..19
            (D) OTHER INFORMATION: /note= "RAP2.8U primer"

(xi) SEQUENCE DESCRIPTION: SEQ ID NO:85:

TCACTCAAAG GCCGAGATC                                                   19

(2) INFORMATION FOR SEQ ID NO:86:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..19
            (D) OTHER INFORMATION: /note= "RAP2.8L primer"

(xi) SEQUENCE DESCRIPTION: SEQ ID NO:86:

TAACAACATC ACCGGCTCG                                                   19

(2) INFORMATION FOR SEQ ID NO:87:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "RAP2.9U primer"

(xi) SEQUENCE DESCRIPTION: SEQ ID NO:87:

GTGAAGGCTT AGGAGGAG                                                    18

(2) INFORMATION FOR SEQ ID NO:88:

(i) SEQUENCE CHARACTERISTICS:
```

```
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "RAP2.9L primer"

(xi) SEQUENCE DESCRIPTION: SEQ ID NO:88:

TGCCTCATAT GAGTCAGAG                                                    19

(2) INFORMATION FOR SEQ ID NO:89:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.10U primer"

(xi) SEQUENCE DESCRIPTION: SEQ ID NO:89:

TCCCGGAGCT TTTAGCCG                                                     18

(2) INFORMATION FOR SEQ ID NO:90:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "RAP2.10L primer"

(xi) SEQUENCE DESCRIPTION: SEQ ID NO:90:

CAACCCGTTC CAACGATCC                                                    19

(2) INFORMATION FOR SEQ ID NO:91:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "RAP2.11U primer"

(xi) SEQUENCE DESCRIPTION: SEQ ID NO:91:

TTCTTCACCA GAAGCAGAGC ATG                                               23

(2) INFORMATION FOR SEQ ID NO:92:
```

```
        (i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..24
            (D) OTHER INFORMATION: /note= "RAP2.11L primer"

(xi) SEQUENCE DESCRIPTION: SEQ ID NO:92:

CTCCATTCAT TGCATATAGG GACG                                              24

(2) INFORMATION FOR SEQ ID NO:93:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..24
            (D) OTHER INFORMATION: /note= "RAP2.12U primer"

(xi) SEQUENCE DESCRIPTION: SEQ ID NO:93:

GCTTTGGTTC AGAACTCGAA CATC                                              24

(2) INFORMATION FOR SEQ ID NO:94:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "RAP2.12L primer"

(xi) SEQUENCE DESCRIPTION: SEQ ID NO:94:

AGGTTGATAA ACGAACGATG CG                                                22

(2) INFORMATION FOR SEQ ID NO:95:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:95:

Lys Lys Ser Arg
1

(2) INFORMATION FOR SEQ ID NO:96:

(i) SEQUENCE CHARACTERISTICS:
            (A) LENGTH: 18 base pairs
            (B) TYPE: nucleic acid
```

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.3 primer"

(xi) SEQUENCE DESCRIPTION: SEQ ID NO:96:

TCATCGCCAC GATCAACC                                                   18

(2) INFORMATION FOR SEQ ID NO:97:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "RAP2.3 primer"

(xi) SEQUENCE DESCRIPTION: SEQ ID NO:97:

AGCAGTCCAA TGCGACGG                                                   18

(2) INFORMATION FOR SEQ ID NO:98:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

Trp Ala Ala Glu Ile Arg Asp
1               5

(2) INFORMATION FOR SEQ ID NO:99:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:99:

Met Ala Asp Ser
1

(2) INFORMATION FOR SEQ ID NO:100:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
```

(B) LOCATION: 1..729
(D) OTHER INFORMATION: /note= "RAP2.1"

(xi) SEQUENCE DESCRIPTION: SEQ ID NO:100:

| | | | | | |
|---|---|---|---|---|---|
| GAAGAGTCTA | CGATGAGAAA | GAGAAGGCAG | CCACCTCAAG | AAGAAGTGCC | TAACCACGTG | 60 |
| GCTACAAGGA | AGCCGTACAG | AGGGATACGG | AGGAGGAAGT | GGGGCAAGTG | GGTGGCTGAG | 120 |
| ATTCGTGAGC | CTAACAAACG | CTCACGGCTT | TGGCTTGGCT | CTTACACAAC | CGATATCGCC | 180 |
| GCCGCTAGAG | CCTACGACGT | GGCCGTCTTC | TACCTCCGTG | GCCCCTCCGC | ACGTCTCAAC | 240 |
| TTCCCTGATC | TTCTCTTGCA | AGAAGAGGAC | CATCTCTCAG | CCGCCACCAC | CGCTGACATG | 300 |
| CCCGCAGCTC | TTATAAGGGA | AAAAGCGGCG | GAGGTCGGCG | CCAGAGTCGA | CGCTCTTCTA | 360 |
| GCTTCTGCCG | CTCCTTCGAT | GGCTCACTCC | ACTCCGCCGG | TAATAAAACC | CGACTTGAAT | 420 |
| CAAATACCCG | AATCCGGAGA | TATATAGTCA | ATTTATATAC | ATGTAGTTTG | TTTTGTTTGA | 480 |
| TTAGAAGATT | ACATTTACAT | ACAAGATACA | CATAGATACT | GGAAAATATA | GGTATGTATA | 540 |
| CATTCATAAA | TTATCTTATG | TATCAAAGAA | TTTTATAGAT | TCTGATTAGC | TTTTTGTTTT | 600 |
| TGTTTTTGAT | AAGAACTCTG | ATTAGTTGTC | CGGAGACAAA | ACCGGCTAAG | AGCAATCCAT | 660 |
| GAGAAGCTAG | CGAGTGTTTT | TTAGTTCAAG | TTGTAATATA | AATGCATATT | AATTCTTTAG | 720 |
| TAATTTTGT | | | | | | 729 |

(2) INFORMATION FOR SEQ ID NO:101:

(i) SEQUENCE CHARACTERISTICS:
(A) LENGTH: 1101 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: -
(B) LOCATION: 1..1101
(D) OTHER INFORMATION: /note= "RAP2.2"

(xi) SEQUENCE DESCRIPTION: SEQ ID NO:101:

| | | | | | |
|---|---|---|---|---|---|
| CGTCCTTGGG | GAAAATGGGC | TGCGGAGATC | CGTGATCCGA | GAAAAGGCTC | CCGAGAATGG | 60 |
| CTTGAACAT | TCGACACTGC | TGAGGAAGCA | GCAAGAGCTT | ATGATGCTGC | AGCACGCAGA | 120 |
| ATCCGTGGCA | CGAAAGCTAA | GGTGAATTTT | CCCGAGGAGA | AGAACCCTAG | CGTCGTATCC | 180 |
| CAGAAACGTC | CTAGTGCTAA | GACTAATAAT | CTTCAGAAAT | CAGTGGCTAA | ACCAAACAAA | 240 |
| AGCGTAACTT | TGGTTCAGCA | GCCAACACAT | CTGAGTCAGC | AGTACTGCAA | CAACTCCTTT | 300 |
| GACAACTCTT | TTGGTGATAT | GAGTTTCATG | GAAGAGAAGC | CTCAGATGTA | CAACAATCAG | 360 |
| TTTGGGTTAA | CAAACTCGTT | CGATGCTGGA | GGTAACAATG | GATACCAGTA | TTTCAGTTCC | 420 |
| GATCAGGGCA | GTAACTCCTT | CGACTGTTCT | GAGTTCGGGT | GGAGTGATCA | CGGCCCTAAA | 480 |
| ACACCCGAGA | TCTCTTCAAT | GCTTGTCAAT | AACAACGAAG | CATCATTTGT | TGAAGAAACC | 540 |
| AATGCAGCCA | AGAAGCTCAA | ACCAAACTCT | GATGAGTCAG | ACGATCTGAT | GGCATACCTT | 600 |
| GACAACGCCT | TGTGGGACAC | CCCACTAGAA | GTGGAAGCCA | TGCTTGGCGC | AGATGCTGGT | 660 |
| GCTGTGACTC | AGGAAGAGGA | AAACCCAGTG | GAGCTATGGA | GCTTAGATGA | GATCAATTTC | 720 |
| ATGCTGGAAG | GAGACTTTTG | AAGTGATCGA | TGGTTCCTTA | GTTTGTAAAT | AAAGCTGTGT | 780 |
| TGGATTTTGC | TGTTGGGGA | TGGTACAAGT | CACACCTCAA | GCTCTATGCA | TTGGTATCTC | 840 |
| ATGAGCCTTC | TCTTCCATAG | AGAGTTTCTC | TTTTAATTTT | GTCGAAATAA | AAAAGGTGTG | 900 |

```
ATGAAGTAAA TAGAGGTATA ATAATATCTA TCTATTAAGT CTTGTTTTGT TCTTTCATTT      960

TTGTATTTCT TTTCTATTTA AAAGACAGTT TATTAGTCTT CTGAGCTCTC TTTTTGATCT     1020

TTGTTATAGC GTATCATCAC CCTCGAAAGT GTAATGTTTT GTACCCCCAA ACTTGTTTAG     1080

CATTATAATA AAGTCTCTTT G                                               1101
```

(2) INFORMATION FOR SEQ ID NO:102:

(i) SEQUENCE CHARACTERISTICS:
        (A) LENGTH: 1055 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1055
        (D) OTHER INFORMATION: /note= "RAP2.3"

(xi) SEQUENCE DESCRIPTION: SEQ ID NO:102:

```
ATAAAGGCAT TCAGCTCCA CCGTAGGAAA CTTTCTCTTG AAAGAAACCC ACAGCAACAA       60

ACAGAGAAAA TGTGTGGCGG TGCTATTATT TCCGATTATG CCCCTCTCGT CACCAAGGCC     120

AAGGGCCGTA AACTCACGGC TGAGGAACTC TGGTCAGAGC TCGATGCTTC CGCCGCCGAC     180

GACTTCTGGG GTTTCTATTC CACCTCCAAA CTCCATCCCA CCAACCAAGT TAACGTGAAA     240

GAGGAGGCAG TGAAGAAGGA GCAGGCAACA GAGCCGGGGA AACGGAGGAA GAGGAAGAAT     300

GTTTATAGAG GGATACGTAA GCGTCCATGG GGAAAATGGG CGGCTGAGAT TCGAGATCCA     360

CGAAAAGGTG TTAGAGTTTG GCTTGGTACG TTCAACACGG CGGAGGAAGC TGCCATGGCT     420

TATGATGTTG CGGCCAAGCA GATCCGTGGT GATAAAGCCA AGCTCAACTT CCCAGATCTG     480

CACCATCCTC CTCCTCCTAA TTATACTCCT CCGCCGTCAT CGCCACGATC AACCGATCAG     540

CCTCCGGCGA AGAAGGTCTG CGTTGTCTCT CAGAGTGAGA GCGAGTTAAG TCAGCCGAGT     600

TTCCCGGTGG AGTGTATAGG ATTTGGAAAT GGGGACGAGT TCAGAACCT GAGTTACGGA      660

TTTGAGCCGG ATTATGATCT GAAACAGCAG ATATCGAGCT TGGAATCGTT CCTTGAGCTG     720

GACGGTAACA CGGCGGAGCA ACCGAGTCAG CTTGATGAGT CCGTTTCCGA GGTGGATATG     780

TGGATGCTTG ATGATGTCAT TGCGTCGTAT GAGTAAAAGA AAAAAAATAA GTTTAAAAAA     840

AGTTAAATAA AGTCTGTAAT ATATATGTAA CCGCCGTTAC TTTTAAAAGG TTTTTACCGT     900

CGCATTGGAC TGCTGATGAT GTCTGTTGTG TAATGTGTAG AATGTGACCA AATGGACGTT     960

ATATTACGGT TTGTGGTATT ATTAGTTTCT TAGATGGAAA AACTTACATG TGTAAATAAG    1020

ATTTGTAATG TAAGACGAAG TACTTATAAC TTCTT                               1055
```

(2) INFORMATION FOR SEQ ID NO:103:

(i) SEQUENCE CHARACTERISTICS:
        (A) LENGTH: 969 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..969
        (D) OTHER INFORMATION: /note= "RAP2.4"

(xi) SEQUENCE DESCRIPTION: SEQ ID NO:103:

```
TCTTCCTCCG ACGCATCACA ACAACAACAA CTCTTTCTCG AATCTTCTCA GCCCAAAGCC       60

GTTACTGATG AAGCAATCTG GAGTCGCTGG ATCTTGTTTC GCTTACGGTT CAGGTGTTCC      120

TTCGAAGCCG ACGAAGCTTT ACAGAGGTGT GAGGCAACGT CACTGGGGAA AATGGGTGGC      180

TGAGATCCGT TTGCCGAGAA ATCGGACTCG TCTCTGGCTT GGGACTTTTG ACACGGCGGA      240

GGAAGCTGCG TTGGCCTATG ATAAGGCGGC GTACAAGCTG CGCGGCGATT TCGCCCGGCT      300

TAACTTCCCT AACCTACGTC ATAACGGATT TCACATCGGA GGCGATTTCG GTGAATATAA      360

ACCTCTTCAC TCCTCAGTCG ACGCTAAGCT TGAAGCTATT TGTAAAAGCA TGGCGGAGAC      420

TCAGAAACAG GACAAATCGA CGAAATCATC GAAGAAACGT GAGAAGAAGG TTTCGTCGCC      480

AGATCTATCG GAGAAAGTGA AGGCGGAGGA GAATTCGGTT TCGATCGGTG GATCTCCACC      540

GGTGACGGAG TTTGAAGAGT CCACCGCTGG ATCTTCGCCG TTGTCGGACT TGACGTTCGC      600

TGACCCGGAG GAGCCGCCGC AGTGGAACGA GACGTTCTCG TTGGAGAAGT ATCCGTCGTA      660

CGAGATCGAT TGGGATTCGA TTCTAGCTTA GGGGCAAAAT AGGAAATTCA GCCGCTTGCA      720

ATGGAGTTTT TGTGAAATTG CATGACTGGC CCAAGAGTAA TTAATTAAAT ATGGATTAGT      780

GTTAAATTTC GTATGTTAAT ATTTGTATTA TGGTTTGTAT TAGTCTCTCT GTGTCGGTCC      840

AGCTTGCGGT TTTTTGTCAG GCTCGACCAT GCCACAGTTT TCATTTTATG TAATCTTTTT      900

TTCTTTTGTC TTATGTAATT TGTAGCTTCA GTTTCTTCAT CTATAATGCA ATTTTATTAT      960

GATTATGTG                                                              969

(2) INFORMATION FOR SEQ ID NO:104:

(i) SEQUENCE CHARACTERISTICS:
        (A) LENGTH: 937 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..937
        (D) OTHER INFORMATION: /note= "RAP2.5"

(xi) SEQUENCE DESCRIPTION: SEQ ID NO:104:

GTCGACCCAC GCGTCCGACT CTCTCTCTAA TCTATCTATC CGAGAATGGC CAAGATGGGC       60

TTGAAACCCG ACCCGGCTAC TACTAACCAG ACCCACAATA ATGCCAAGGA GATTCGTTAC      120

AGAGGCGTTA GGAAGCGTCC TTGGGGCCGT TATGCCGCCG AGATCCGAGA TCCGGGCAAG      180

AAAACCCGCG TCTGGCTTGG CACTTTCGAT ACGGCTGAAG AGGCGGCGCG TGCTTACGAT      240

ACGGCGGCGC GTGATTTTCG TGGTGCTAAG GCTAAGACCA ATTTCCCAAC TTTTCTCGAG      300

CTGAGTGACC AGAAGGTCCC TACCGGTTTC GCGCGTAGCC CTAGCCAGAG CAGCACGCTC      360

GACTGTGCTT CTCCTCCGAC GTTAGTTGTG CCTTCAGCGA CGGCTGGGAA TGTTCCCCCG      420

CAGCTCGAGC TTAGTCTCGG CGGAGGAGGC GGCGGCTCGT GTTATCAGAT CCCGATGTCG      480

CGTCCTGTCT ACTTTTTGGA CCTGATGGGG ATCGGTAACG TAGGTCGTGG TCAGCCTCCT      540

CCTGTGACAT CGGCGTTTAG ATCGCCGGTG GTGCATGTTG CGACGAAGAT GGCTTGTGGT      600

GCCCAAAGCG ACTCTGATTC GTCATCGGTC GTTGATTTCG AAGGTGGGAT GGAGAAGAGA      660

TCTCAGACTG TTAGATCTAG ATCTTAATTT GCCTCCTCCA TCGGAACAGG CCTGAGCTTT      720

TAACGGTGTC GTTTCAATTC GAAGCGCATG CGTTTCTTCT TCTTTTTGAG CTGTGAAAAT      780
```

```
TCGTTTTCTC ATAGTTTTTC CTCTCTCTCT CTCTCAGTCT AAATTTATTA CCAGTTTTTA    840

GAAAGAAAAA ACAGATTAAA TCTGAGAGAG AAAAATATAA TTTTAGCTGA CATGGATCGT    900

TATGTACATA TTATTACATA ACCGGAGATC TGAACTG                             937
```

(2) INFORMATION FOR SEQ ID NO:105:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..651
        (D) OTHER INFORMATION: /note= "RAP2.6"

(xi) SEQUENCE DESCRIPTION: SEQ ID NO:105:

```
AAGAGAAGAG TTTTCTTTGC CTCCTCAACC ATTGATTACC GGTTCAGCTG TGACTAAAGA     60

ATGTGAAAGC TCAATGTCCT TGGAGAGGCC AAAAAAATAT AGAGGAGTAA GGCAACGACC    120

ATGGGGAAAA TGGGCGGCGG AGATTCGAGA CCCACACAAG GCGACACGTG TATGGCTTGG    180

GACATTCGAG ACAGCCGAGG CCGCCGCAAG AGCCTATGAT GCGGCAGCAC TTCGCTTTAG    240

AGGAAGCAAA GCAAAGCTTA ATTTCCCCGA AAATGTTGGA ACTCAGACGA TTCAACGAAA    300

TTCTCATTTC TTGCAAAACT CAATGCAACC TTCTCTAACA TACATCGATC AATGTCCAAC    360

TCTATTATCT TACTCTCGAT GTATGGAGCA ACAACAACCA TTAGTAGGCA TGTTGCAGCC    420

AACAGAGAG GAAAATCACT TTTTCGAAAA ACCATGGACC GAATATGATC AATACAATTA     480

CTCCTCTTTT GGTTAACTAA CATATCGTCA ACGCTTTGTA TTTCTACTTA TTCGATCTAC    540

CAATTTTTTC TCTCCCAATA CAACTTCAGT CTGATTATTG CCTTCTTAGA TATGTCTTCG    600

AATGTTATGA CTATACATGG GTGTATATAA AATTTGTGAT CAAAGTCTTG T             651
```

(2) INFORMATION FOR SEQ ID NO:106:

(i) SEQUENCE CHARACTERISTICS:
        (A) LENGTH: 1329 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1329
        (D) OTHER INFORMATION: /note= "RAP2.7"

(xi) SEQUENCE DESCRIPTION: SEQ ID NO:106:

```
AATGCCGATG GAGACGAAGA CTCTTGCTCT ACTCGAGCTT TCACTCTCAG TTTCGATATT     60

TTAAAAGTCG GAAGTAGTAG CGGCGGAGAC GAAAGCCCCG CCGCTTCAGC TTCCGTTACT    120

AAAGAGTTTT TTCCGGTGAG TGGAGACTGT GGACATCTAC GAGATGTTGA AGGATCATCA    180

AGCTCTAGAA ACTGGATAGA TCTTTCTTTT GACCGTATTG GTGACGGAGA AACGAAATTG    240

GTAACTCCGG TTCCGACTCC GGCTCCGGTT CCGGCTCAGG TTAAAAAGAG TCGGAGAGGA    300

CCAAGGTCTA GAAGTTCACA GTATAGAGGA GTTACTTTTT ATAGAAGAAC TGGTCGATGG    360

GAGTCACATA TTTGGGATTG TGGGAAACAA GTTTATTTAG GTGGTTTCGA CACTGCTCAT    420

GCTGCAGCTA GAGCTTATGA TCGAGCTGCT ATTAAATTTA GAGGTGTTGA TGCTGATATC    480
```

```
AACTTTACTC TTGGTGATTA TGAGGAAGAT ATGAAACAGG TACAAAACTT GAGTAAGGAA      540

GAGTTTGTGC ATATACTGCG TAGACAGAGC ACGGGGTTTT CGCGGGGGAG TTCGAAGTAT      600

CGAGGGGTTA CGTTACACAA ATGTGGTAGA TGGGAAGCTA GGATGGGGCA GTTTCTTGGT      660

AAAAAGGCTT ATGACAAGGC TGCAATCAAC ACTAATGGTA GAGAAGCAGT CACGAACTTC      720

GAGATGAGTT CATACCAAAA TGAGATTAAC TCTGAGAGCA ATAACTCTGA GATTGACCTC      780

AACTTGGGAA TCTCTTTATC GACCGGTAAT GCGCCAAAGC AAAATGGGAG GCTCTTTCAC      840

TTCCCTTCTA ATACTTATGA AACTCAGCGT GGAGTTAGCT TGAGGATAGA TAACGAATAC      900

ATGGGAAAGC CGGTGAATAC ACCTCTTCCT TATGGATCCT CGGATCATCG CCTTTACTGG      960

AACGGAGCAT GCCCGAGTTA TAATAATCCC GCCGAGGGAA GAGCAACAGA AAAGAGAAGT     1020

GAAGCTGAAG GGATGATGAG TAACTGGGGA TGGCAGAGAC CGGGGCAAAC AAGCGCCGTG     1080

AGACCGCAGC CACCGGGACC ACAACCACCA CCATTGTTCT CAGTTGCAGC AGCATCATCA     1140

GGATTCTCAC ATTTCCGGCC ACAACCTCCC AATGACAATG CAACACGTGG TTACTTTTAT     1200

CCACACCCTT AACTTGTAAG GGACATATG  AGAGTTTTTT TACCATCTCT CTCTCTCTCA     1260

ACACTCTAGT CCCCTTTCAA AAATGTCATT TGGGTTTTAG ATTTTTCACA TACAATGATC     1320

AATTTTTCC                                                             1329

(2) INFORMATION FOR SEQ ID NO:107:

(i) SEQUENCE CHARACTERISTICS:
        (A) LENGTH: 1113 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1113
        (D) OTHER INFORMATION: /note= "RAP2.8"

(xi) SEQUENCE DESCRIPTION: SEQ ID NO:107:

CGCCACCACC GCCAAGAAGC TCTCTCCTCC TCCCGCGGCG GCGTTACGCC TCTACCGGAT       60

GGGAAGCGGC GGGAGCAGCG TCGTGTTGGA TCCCGAGAAC GGCCTAGAGA CGGAGTCACG      120

AAAGCTACCA TCTTCAAAAT ACAAAGGTGT TGTTCCTCAG CCTAACGGAA GATGGGGAGC      180

TCAGATCTAC GAGAAGCACC AACGAGTATG GCTCGGGACT TCAACGAGC  AAGAAGAAGC      240

TGCTCGTTCC TACGACATCG CAGCTTGTAG ATTCCGTGGC CGCGACGCCG TCGTCAACTT      300

CAAGAACGTT CTGGAAGACG GCGATTTAGC TTTTCTTGAA GCTCACTCAA AGGCCGAGAT      360

CGTCGACATG TTGAGAAAAC ACACTTACGC CGACGAGCTT GAACAGAACA ATAAACGGCA      420

GTTGTTTCTC TCCGTCGACG CTAACGGAAA ACGTAACGGA TCGAGTACTA CTCAAAACGA      480

CAAAGTTTTA AAGACGTGTG AAGTTCTTTT CGAGAAGGCT GTTACACCTA GCGACGTTGG      540

GAAGCTAAAC CGTCTCGTGA TACCTAAACA ACACGCCGAG AAACACTTTC CGTTACCGTC      600

ACCGTCACCG GCAGTGACTA AAGGAGTTTT GATCAACTTC GAAGACGTTA ACGGTAAAGT      660

GTGGAGGTTC CGTTACTCAT ACTGGAACAG TAGTCAAAGT TACGTGTTGA CCAAGGGATG      720

GAGTCGATTC GTCAAGGAGA AGAATCTTCG AGCCGGTGAT GTTGTTACTT TCGAGAGATC      780

GACCGGACTA GAGCGGCAGT TATATATTGA TTGGAAAGTT CGGTCTGGTC CGAGAGAAAA      840

CCCGGTTCAG GTGGTGGTTC GGCTTTTCGG AGTTGATATC TTTAATGTGA CCACCGTGAA      900
```

```
GCCAAACGAC GTCGTGGCCG TTTGCGGTGG AAAGAGATCT CGAGATGTTG ATGATATGTT      960

TGCGTTACGG TGTTCCAAGA AGCAGGCGAT AATCAATGCT TTGTGACATA TTTCCTTTTC     1020

CGATTTTATG CTTTCGTTTT TTAATTTTTT TTTTTGTCAA GTTGTGTAGG TTGTGATTCA     1080

TGCTAGGTTG TATTTAGGAA AAGAGATAAG ACC                                  1113
```

(2) INFORMATION FOR SEQ ID NO:108:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..417
        (D) OTHER INFORMATION: /note= "RAP2.9"

(xi) SEQUENCE DESCRIPTION: SEQ ID NO:108:

```
CGATCACGGA TCTGGCTTGG TTCATACAAA ACCGCCGTTG CCGCGGCACG GGCCTACGAT       60

ACCGCTGTGT TTTACTTACG TGGTCCTTCG GCGAGACTCA ATTTCCCTGA AGAGGTCTTT      120

AAGGATGGAA ACGGCGGTGA AGGCTTAGGA GGAGATATGT CTCCGACGTT GATACGGAAG      180

AAGGCGGCTG AGGTGGGAGC TAGAGTCGAC GCAGAGTTGC GGTTAGAGAA TAGGATGGTT      240

GAGAACTTAG ACATGAATAA GTTGCCGGAG GCATATGGAT TGTAATTTAT AGTTTGGTAG      300

TTTATAGGTT GGAGATTGCC CGGAGACAGA GTCAAACAGA GGTTCTCTGA CTCATATGAG      360

GCATAATATA GTTAATATAG TAATTTTTGT TTTGAGCATA GTAATTATGT CATAACC        417
```

(2) INFORMATION FOR SEQ ID NO:109:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..814
        (D) OTHER INFORMATION: /note= "RAP2.10"

(xi) SEQUENCE DESCRIPTION: SEQ ID NO:109:

```
ATTTTTTGAA ACTTCTTCTC TTTTGCGGTT TCGTGTTCCA CTCCTCTCTT CTTGGCCCAC       60

GTGTTCATCA ATCTCTCCCT CCGCATGTAA TCGCTTCGCC GTCAATATCA CATCTTTCTT      120

CTTCTTTATC TTTAAAATCT CTTTAGATCG ATTCTTTTGT GGATTCTTGA AATCTCCGGA      180

GAAAACCACT ATGGAGACGG CGACTGAAGT GGCCACGGTG GTGTCAACTC CGGCGGTTAC      240

GGTTGCGGCG GTGGCGACGA GGAAGAGAGA TAAGCCGTAT AAAGGGATAA GGATGAGGAA      300

GTGGGGGAAG TGGGTGGCGG AGATAAGAGA GCCTAATAAA AGGTCAAGGA TCTGGCTTGG      360

CTCTTACTCT ACTCCTGAAG CGGCGGCGCG TGCTTACGAC ACGGCGGTGT TTTATCTCCG      420

AGGTCCTTCT GCTCGGCTTA ACTTCCCGGA GCTTTTAGCC GGAGTGACGG TGACGGGAGG      480

AGGCGGAGGA GGAGTGAACG GTGGTGGAGA TATGTCGGCG GCGTATATAA GGAGAAAAGC      540

GGCGGAGGTT GGAGCACAAG TGGATGCGTT AGAAGCGGCG GGGGCGGGAG GGAATCGTCA      600

TCATCATCAT CATCAACATC AACGTGGTAA TCATGATTAC GTAGATAATC ATAGTGATTA      660
```

```
TCGTATTAAT GATGATCTTA TGGAGTGTAG TAGTAAAGAA GGGTTTAAGA GGTGTAATGG        720

ATCGTTGGAA CGGGTTGATT TAAACAAATT ACCCGATCCG GAAACTTCAG ATGACGATTA        780

GGAAAGCAAA AATAGAAAC AAAAAAAAAA AAAA                                    814
```

(2) INFORMATION FOR SEQ ID NO:110:

(i) SEQUENCE CHARACTERISTICS:
        (A) LENGTH: 933 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..933
        (D) OTHER INFORMATION: /note= "RAP2.11"

(xi) SEQUENCE DESCRIPTION: SEQ ID NO:110:

```
AAAAAAATAT GGAACATCAA ACAACTCCAA AGCAGAAAAC TAAGGAGAAG AGCAAAGGCA         60

ACAAGACTAA GTTTGTGGGA GTTAGGCAAA GGCCTTCAGG AAAATGGGTG GCAGAGATCA        120

AAGCACACTAC ACAAAAGATA CGGATGTGGC TCGGAACCTT TGAAACCGCA GAAGAAGCCG       180

CTCGAGCCTA CGATGAAGCT GCATGTCTCT TACGTGGCTC CAATACTCGC ACCAATTTCG        240

CAAACCATTT TCCTAACAAC TCACAACTAT CTTTGAAGAT CAGAAATCTT CTTCACCAGA        300

AGCAGAGCAT GAAGCAGCAG CAACAACAAC AACACAAACC AGTTTCTTCT TTAACGGATT        360

GCAACATCAA CTACATCTCG ACTGCTACTA GTCTCACCAC AACCACCACC ACCACCACTA        420

CCACGGCCAT ACCGCTCAAT AATGTGTACC GACCAGATTC ATCGGTCATT GGGCAACCAG        480

AAACCGAGGG TCTCCAGCTT CCTTATTCGT GGCCCCTTGT CTCTGGATTC AACCATCAGA        540

TTCCATTGGC TCAGGCAGGG GGAGAAACAC ATGGACATCT CAACGATCAC TACTCAACCG        600

ATCAACATTT GGGTCTTGCA GAAATTGAAA GACAGATATC TGCGTCCCTA TATGCAATGA        660

ATGGAGCTAA CAGTTACTAT GACAACATGA ATGCAGAATA TGCAATTTTC GATCCTACCG        720

ATCCCATTTG GGATCTCCCT TCACTCTCCC AACTCTTCTG CCCTACGTGA TTTCCAATTT        780

ACTTTTCCTG ATCAATTCAT GTAATGTTTG GATCAATGAT CCATGATTGT AAAGTAGAAC        840

ACATCTCTAC AATGTTCCAA TAGACAAGAT TGTACCTAAA GAAAATGGAC AATGTAAGAA        900

GATAATGAAG GTTTCGTACA ACAAAAGCTT GAT                                    933
```

(2) INFORMATION FOR SEQ ID NO:111:

(i) SEQUENCE CHARACTERISTICS:
        (A) LENGTH: 1277 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1277
        (D) OTHER INFORMATION: /note= "RAP2.12"

(xi) SEQUENCE DESCRIPTION: SEQ ID NO:111:

```
CGTTCGAATT TCTTCGATTT TGACGCTGAG TTCGAAGCTG ATTTCCAAGG TTTCAAAGAT         60

GATTCGTCTA TCGATTGCGA TGATGATTTC GACGTCGGTG ATGTTTTCGC CGATGTGAAA       120
```

-continued

| | | | | | |
|---|---|---|---|---|---|
|CCATTCGTTT|TCACTTCGAC|TCCAAAACCC|GCCGTCTCCG|CCGCTGCGGA|AGGTTCAGTT 180|
|TTTGGTAAGA|AAGTTACTGG|CTTGGATGGG|GACGCTGAGA|AATCTGCAAA|TAGGAAGAGG 240|
|AAGAATCAGT|ACCGAGGGAT|TAGGCAACGT|CCTTGGGGAA|AATGGGCTGC|TGAGATACGT 300|
|GATCCAAGGG|AAGGTGCTAG|AATCTGGCTT|GGAACGTTCA|AGACAGCTGA|GGAAGCTGCT 360|
|AGAGCTTACG|ATGCTGCAGC|GCGGAGAATC|CGTGGATCTA|AAGCTAAGGT|GAATTTCCCT 420|
|GAAGAAAACA|TGAAGGCTAA|TTCTCAGAAA|CGCTCTGTGA|AGGCTAATCT|TCAGAAACCA 480|
|GTGGCTAAAC|CTAACCCTAA|CCCAAGTCCA|GCTTTGGTTC|AGAACTCGAA|CATCTCCTTT 540|
|GAAAATATGT|GTTTCATGGA|GGAGAAACAC|CAAGTGAGCA|ACAACAACAA|CAACCAGTTT 600|
|GGGATGACAA|ACTCCGTTGA|TGCTGGATGT|AATGGGTATC|AGTATTTCAG|CTCTGACCAG 660|
|GGTAGTAATT|CTTTCGATTG|TTCGGAGTTT|GGTTGGAGCG|ATCAAGCTCC|GATAACTCCC 720|
|GACATCTCTT|CTGCGGTTAT|CAACAACAAC|AACTCAGCTC|TGTTCTTTGA|GGAAGCCAAT 780|
|CCAGCTAAGA|AGCTCAAGTC|TATGGATTTC|GAGACACCTT|ACAACAACAC|TGAATGGGAC 840|
|GCTTCACTGG|ATTTCCTCAA|CGAAGATGCT|GTAACGACTC|AGGACAATGG|TGCAAACCCT 900|
|ATGGACCTAT|GGAGTATTGA|TGAAATTCAT|TCCATGATTG|GAGGAGTCTT|CTGAAGAGAT 960|
|CCAGTTTCAT|GTAAATAAGG|CTGCATGTTT|GTGAGTTTCC|CGCATCGTTC|GTTTATCAAC 1020|
|CTCCAAAACT|TTCTAATGTC|TGTTACTTGC|ATCTTCTTCT|GCTGTCTCTG|TCTGTCTCTC 1080|
|TCAGGAGTTC|CTGTTTGCAT|TGCGAGAAGC|CATGAGCCTC|TATCTTGAGG|GTAGTTGTGA 1140|
|TGAAGTTAAG|TAGAGGCTTA|TTTTTAGGGG|TTGTGGTAGT|TTTTGTTTTA|GTGAATCTTT 1200|
|TGAATTCGTT|TGTGTTTTGT|TTTTGTTACT|TTATGCCCCA|AAACTCCTTT|AACATTTGTC 1260|
|ATAATGTGTT|TGAACCT| | | | 1277|